United States Patent
Bray et al.

(10) Patent No.: US 8,100,976 B2
(45) Date of Patent: *Jan. 24, 2012

(54) IMPLANT SUBSIDENCE CONTROL

(75) Inventors: Robert S Bray, Studio, CA (US); James M Moran, North Royalton, OH (US); Mark T. Whiteaker, Rocky River, OH (US)

(73) Assignee: RSB Spine LLC, Cleveland, OH (US)

( * ) Notice: Subject to any disclaimer, the term of this patent is extended or adjusted under 35 U.S.C. 154(b) by 1420 days.

This patent is subject to a terminal disclaimer.

(21) Appl. No.: 11/620,255

(22) Filed: Jan. 5, 2007

(65) Prior Publication Data

US 2007/0106384 A1    May 10, 2007

Related U.S. Application Data

(63) Continuation-in-part of application No. 11/248,651, filed on Oct. 12, 2005, which is a continuation of application No. 10/419,652, filed on Apr. 21, 2003, now Pat. No. 6,984,234.

(51) Int. Cl.
*A61F 2/44* (2006.01)

(52) U.S. Cl. .................. 623/17.16; 623/17.11

(58) Field of Classification Search .... 623/17.11–17.16; 606/280–299, 70, 71, 246, 249
See application file for complete search history.

(56) References Cited

U.S. PATENT DOCUMENTS

| | | | |
|---|---|---|---|
| 4,904,261 A | 2/1990 | Dove et al. | |
| 5,306,309 A * | 4/1994 | Wagner et al. | 623/17.16 |
| 5,364,399 A | 11/1994 | Lowery et al. | |
| 5,713,898 A | 2/1998 | Stucker et al. | |
| 5,713,899 A | 2/1998 | Marnay et al. | |
| 5,800,433 A | 9/1998 | Benzel et al. | |
| 6,066,175 A | 5/2000 | Henderson et al. | |
| 6,080,193 A | 6/2000 | Hochshuler et al. | |
| 6,190,413 B1 * | 2/2001 | Sutcliffe | 623/17.11 |
| 6,193,721 B1 | 2/2001 | Michelson | |
| 6,413,259 B1 | 7/2002 | Lyons et al. | |
| 6,461,359 B1 | 10/2002 | Tribus et al. | |
| 6,520,993 B2 * | 2/2003 | James et al. | 623/17.16 |
| 6,524,311 B2 | 2/2003 | Gaines, Jr. | |
| 6,533,786 B1 | 3/2003 | Needham et al. | |
| 6,572,622 B1 | 6/2003 | Schafer et al. | |

(Continued)

FOREIGN PATENT DOCUMENTS

EP    1103236 A2    11/2000

(Continued)

OTHER PUBLICATIONS

International Search Report (PCT/US2007/087108) dated Dec. 15, 2008.

*Primary Examiner* — Eduardo C Robert
*Assistant Examiner* — Jan Christopher Merene
(74) *Attorney, Agent, or Firm* — Pearne & Gordon LLP

(57) ABSTRACT

An interbody device for the fixation and support of adjacent bone bodies includes a body for implantation at a location between the two vertebrae and one or more protrusions extending from the body. The protrusion(s) are configured for engagement with one of the vertebrae upon implantation and for progressive penetration into the vertebra over a period of time subsequent to the implantation.

58 Claims, 23 Drawing Sheets

U.S. PATENT DOCUMENTS

| | | |
|---|---|---|
| 6,579,290 B1 | 6/2003 | Hardcastle et al. |
| 6,629,998 B1 | 10/2003 | Lin |
| 6,656,179 B1 | 12/2003 | Schaefer et al. |
| 6,682,563 B2 * | 1/2004 | Scharf ................ 623/17.16 |
| 6,730,127 B2 | 5/2004 | Michelson |
| 6,755,833 B1 * | 6/2004 | Paul et al. ................ 606/70 |
| 6,837,905 B1 | 1/2005 | Lieberman |
| 6,884,242 B2 | 4/2005 | LeHuec et al. |
| 7,041,135 B2 | 5/2006 | Michelson |
| 7,163,561 B2 | 1/2007 | Michelson |
| 7,232,464 B2 | 6/2007 | Mathieu et al. |
| 7,320,708 B1 | 1/2008 | Bernstein |
| 2002/0004683 A1 * | 1/2002 | Michelson ............. 623/17.16 |
| 2002/0016595 A1 | 2/2002 | Michelson |
| 2002/0082597 A1 | 6/2002 | Fraser |
| 2002/0087212 A1 * | 7/2002 | James et al. ............ 623/17.11 |
| 2002/0120273 A1 * | 8/2002 | Needham et al. ........... 606/61 |
| 2002/0138142 A1 * | 9/2002 | Castro et al. ............ 623/17.11 |
| 2003/0078668 A1 * | 4/2003 | Michelson ............. 623/17.16 |
| 2003/0167091 A1 | 9/2003 | Scharf |
| 2003/0225409 A1 | 12/2003 | Freid et al. |
| 2004/0127902 A1 | 7/2004 | Suzuki et al. |
| 2004/0193269 A1 | 9/2004 | Fraser et al. |
| 2004/0204712 A1 | 10/2004 | Kolb et al. |
| 2004/0236333 A1 | 11/2004 | Lin |
| 2005/0101960 A1 * | 5/2005 | Fiere et al. ................ 606/72 |
| 2005/0177236 A1 | 8/2005 | Mathieu et al. |
| 2006/0030851 A1 | 2/2006 | Bray et al. |
| 2006/0085071 A1 | 4/2006 | Lechmann et al. |

FOREIGN PATENT DOCUMENTS

| | | |
|---|---|---|
| EP | 1247503 A2 | 3/2002 |
| WO | 9720526 | 6/1997 |
| WO | 9856319 | 12/1998 |
| WO | WO 98/58604 | 12/1998 |
| WO | 9927864 A2 | 6/1999 |
| WO | 0007527 | 2/2000 |
| WO | 0066011 A1 | 11/2000 |
| WO | 0066045 | 11/2000 |
| WO | 0180785 A1 | 11/2001 |
| WO | 0195837 | 12/2001 |
| WO | 0203885 A2 | 1/2002 |
| WO | WO 03/005938 | 1/2003 |
| WO | 2004069106 A1 | 8/2004 |
| WO | WO 2004/069106 | 8/2004 |

* cited by examiner

IMPLANT SUBSIDENCE CONTROL

RELATED PATENT APPLICATION

This application is a continuation-in-part of U.S. patent application Ser. No. 11/248,651, filed Oct. 12, 2005, which claims priority to U.S. patent application Ser. No. 10/419,652, filed Apr. 21, 2003, which issued as U.S. Pat. No. 6,984,234. The contents of each of the aforementioned patent and patent application are incorporated herein by reference in their entirety.

BACKGROUND OF THE INVENTION

1. Field of the Invention

The present invention relates generally to devices for the fixation and support of bone bodies. In particular, the present invention relates to an implant device, such as an interbody fusion device, having subsidence control.

2. Background of the Invention

Bone mechanical properties greatly influence the stiffness of vertebra-implant-vertebra constructs. Bone properties are a function of many factors including bone mineral density, age, and sex. For comparative purposes, it will be assumed that bone properties are constant in the following discussions. Preparation of the bone to receive the implant can influence strength and stiffness. Again, for comparative purposes, it will be assumed that bone preparation is not a variable except when specifically discussed.

Interbody devices are typically classified as threaded cylinders or screws (e.g., BAK C), boxes (usually tapered rectangular boxes with ridges like the Brantigan cage), or vertical cylinders (e.g., Harms cage). Threaded cylinders usually have small pores and graft material is located inside the hollow interior of the cylinder. Device stiffness might be an issue for such designs. Boxes and vertical cylinders are generally open structures and in these devices a combination of device stiffness and subsidence are responsible for loading the graft.

The stiffness of a material and the stiffness of the structure (device) are often confused. Material stiffness is quantified by Modulus of Elasticity, the slope of the stress-strain curve. Steel has a high modulus, and gold has a low modulus. Structural or device stiffness is a function of dimensions of the part and the material from which the part is made. For example, steel is a very stiff material. However, when formed into the shape of a structure like a paperclip it is easily bent. Stiffness of an assembly or construct can be influenced by connections. While a paperclip and even a piece of paper are strong in tension, when assembled with a piece of paper a paperclip can be easily pulled off because they are only held together by friction.

The same analogy holds for inter-vertebral implants. For instance, consider a simplified construct consisting of a bone block, an interbody device, and a bone block, stacked on top of each other and loaded in compression. If the device is made from a low modulus material but has a large footprint on the bone, and conforms very well to the bone, the assembly can be very stiff in compression. The slope of the load-deflection curve would be steep. A device made from a high modulus material that has a small footprint on the bone and sharp edges might simply punch into the bone under compressive load. The slope of the load-deflection curve would be low, making the construct appear very compliant despite the fact that the device is rigid.

Finally, the terms flexibility and stiffness are used in connection with both the range of motion of the spine and the mechanical performance of implant constructs, and the distinction is not always clearly defined.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with an aspect of the present invention, an interbody device is provided. The interbody device includes a base member comprising a primary member and a secondary member. The primary member has a top and bottom surface and the secondary member extends downward from a bottom surface of the primary member at an angle relative thereto. The primary member further includes a plurality of interface members extending from at least one surface thereon, the interface members being configured to provide controlled subsidence of the interbody device into at least one bone body. The primary member further includes at least one angled aperture which comprises an elongated slot configured to receive a bone fastener therethrough. The secondary member includes at least one angled aperture configured to receive a bone fastener therethrough. The interbody device also includes a plurality of bone fasteners extending through apertures provided in the base member.

In accordance with another aspect of the present invention, the interbody device includes a base member comprising a primary member and a secondary member. The primary member has a top and bottom surface and the secondary member extends downward from the bottom surface of the primary member at an angle relative thereto. The primary member further includes a plurality of interface members extending from at least one surface thereon, the interface members being configured to provide controlled subsidence of the interbody device into at least one bone body. The primary member further includes at least one angled aperture which comprises a hole configured to receive a bone fastener therethrough. The secondary member includes at least one angled aperture comprising a hole configured to receive a bone fastener therethrough. The interbody device also includes a plurality of bone fasteners extending through apertures provided in the base member.

In accordance with another aspect of the present invention, the interbody device includes a base member comprising a primary member and a secondary member. The primary member has a top and bottom surface and the secondary member extends upward from the top surface of the primary member at an angle relative thereto. The primary member further includes a plurality of interface members extending from at least one surface thereon, the interface members being configured to provide controlled subsidence of the interbody device into at least one bone body. The primary member further includes at least one angled aperture configured to receive a bone fastener therethrough. The secondary member includes at least one angled aperture which configured to receive a bone fastener therethrough. The interbody device also includes a plurality of bone fasteners extending through apertures provided in the base member.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

The foregoing and other features and advantages of the present invention will become apparent to those skilled in the art to which the present invention relates upon reading the following description with reference to the accompanying drawings.

DESCRIPTION OF EXAMPLE EMBODIMENTS

Figure 1:
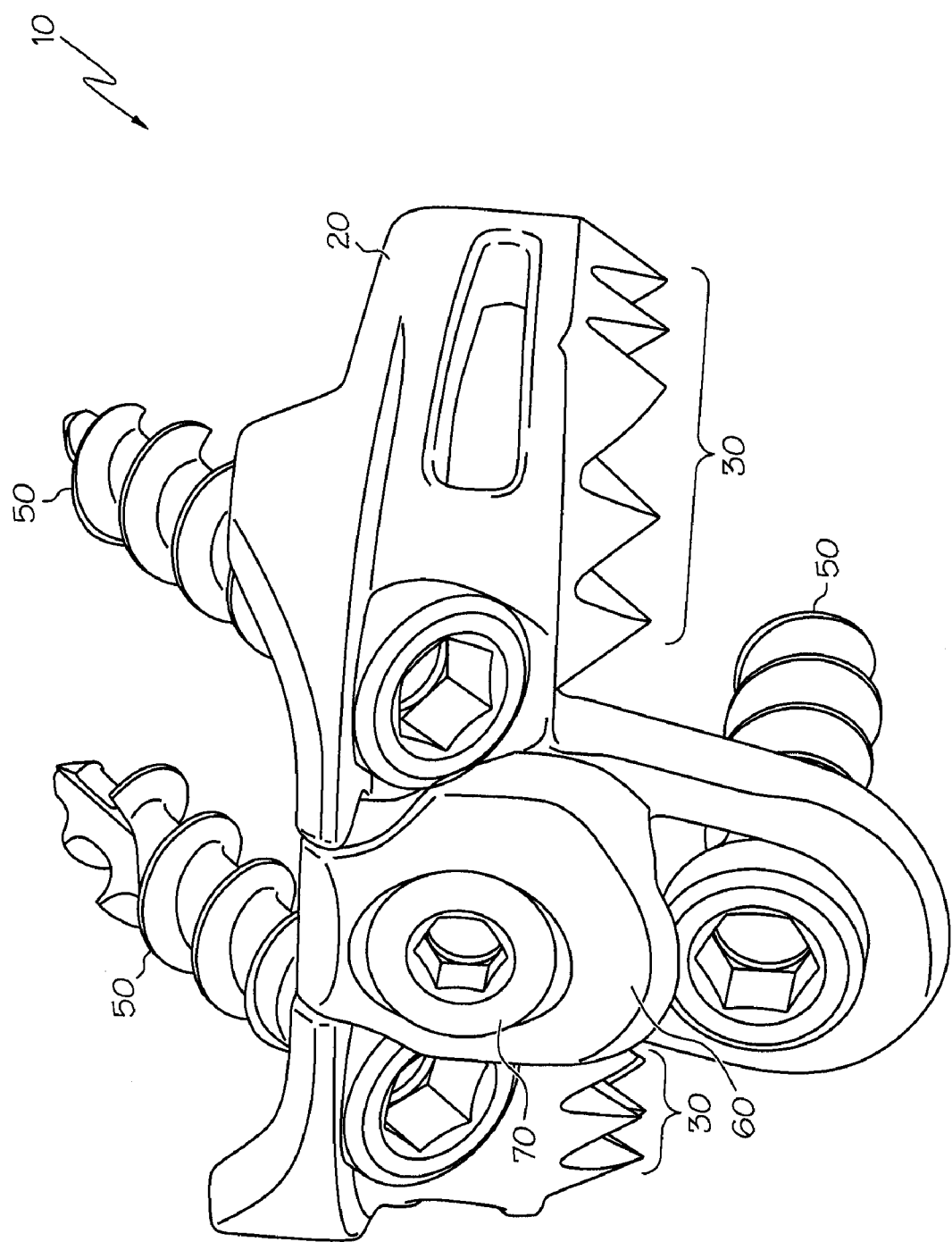
FIG. 1 is a front perspective view of an interbody device in accordance with an aspect of the present invention.

The present invention relates to an implant device, such as an interbody device, having subsidence control. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

Figure 2:
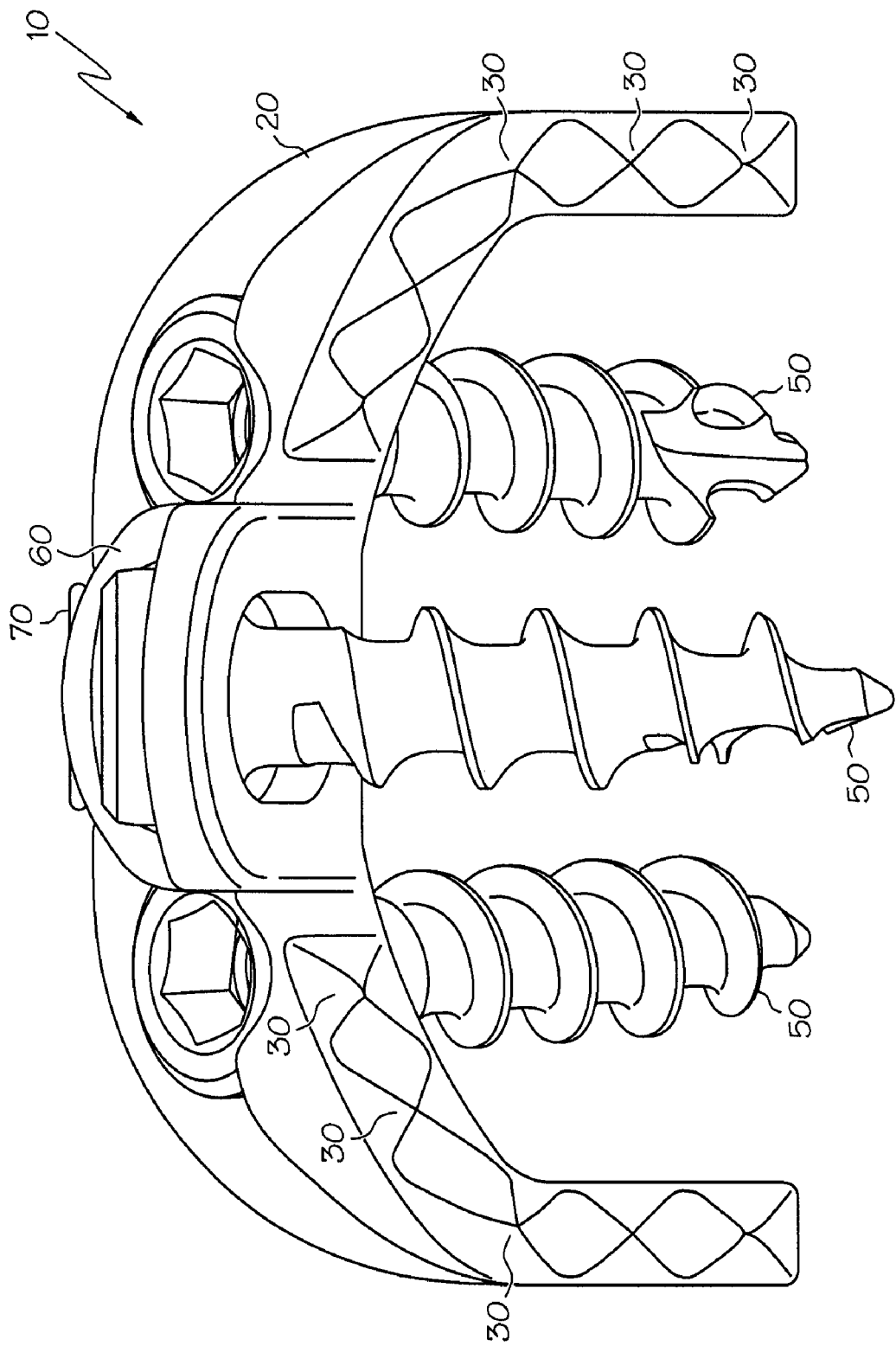
FIG. 2 is a bottom perspective view of an interbody device in accordance with an aspect of the present invention.
Figure 3:
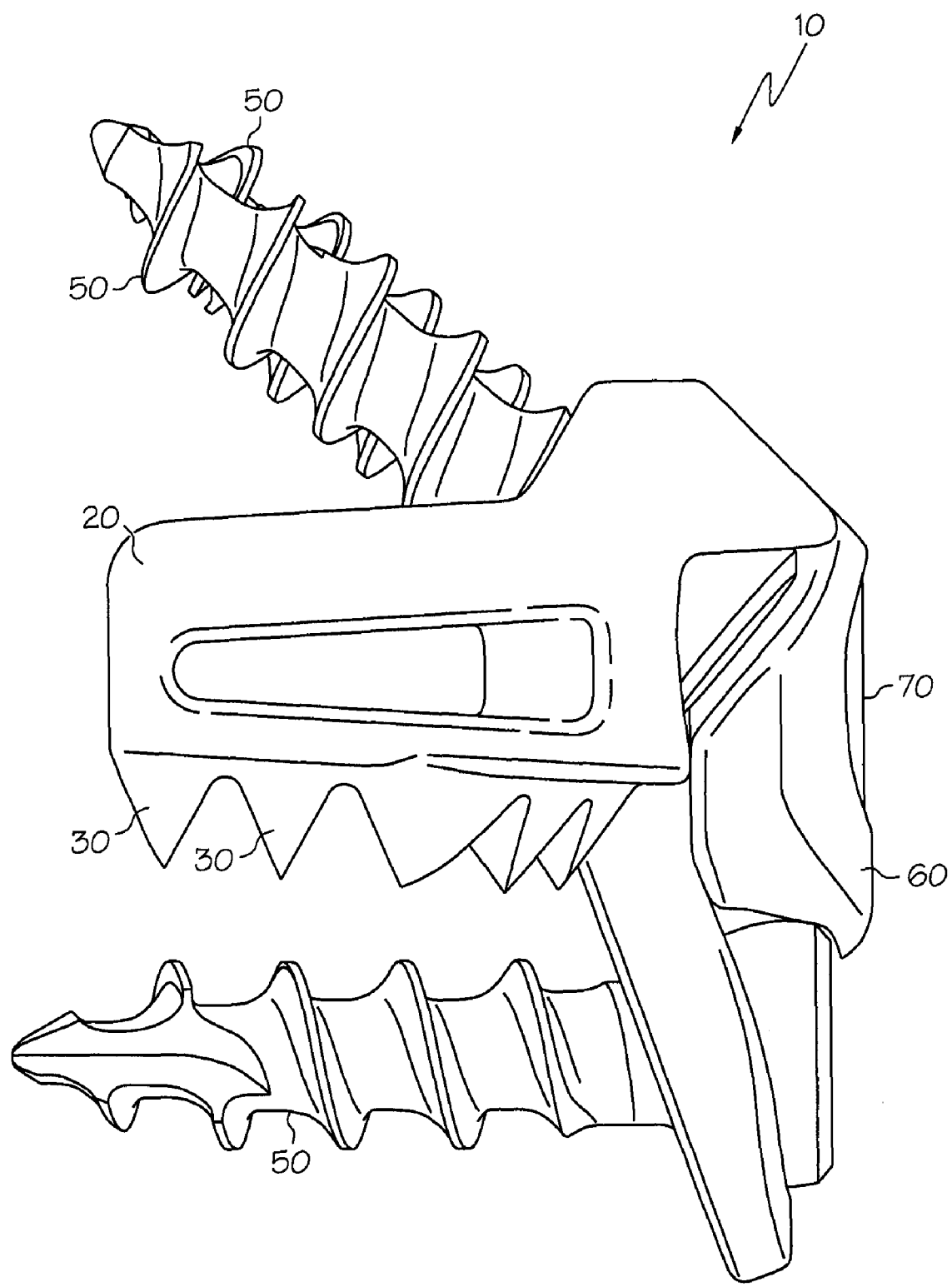
FIG. 3 is a side view of an interbody device in accordance with an aspect of the present invention.

Referring initially to FIGS. 1-3, an example of an interbody device 10 is illustrated in accordance with an aspect of the present invention. The interbody device 10 is configured to fix and secure two bone bodies. As used herein, the phrase "bone bodies" is intended to include individual bones as well as fragments or portions of bones. More specifically, and as will be described in further detail below, the interbody device can fix and secure adjacent vertebrae that have had cartilaginous disc between the vertebrae replaced with a graft of bone tissue or some other material that promotes the fusion of the vertebrae. It is to be appreciated that one aspect that is addressed by the present invention is load sharing with a graft. The configuration of the interbody device 10 includes a base member 20 having a plurality of protrusions or interface members 30 extending from a portion of the base member 20. As will be explained in further detail below, the interface members 30 are configured to contact at least one surface of at least one bone body to provide subsidence control for the interbody device 10. Controlled subsidence relates to resistance to subsidence and total amount of subsidence. The base member 20 of the interbody device 10 also includes a plurality of apertures, each of which is configured to receive a corresponding bone fastener 50 therethrough.

The interbody device 10 also includes a restraining means for restricting movement of one or more bone fasteners 50 coupled to the base member 20. The restraining means can be any means for securely covering at least a part of each of the bone fasteners 50 so that the bone fasteners 50 cannot back out from the bone bodies once screwed in through the base member 20 of the device 10. In the depicted embodiment, the bone screw restraining means comprises a restraining plate 60 and a restraining plate fixing means 70.

Turning now to FIGS. 4-7, the base member 20 of the interbody device 10 is illustrated in greater detail. The base member 20 is generally u-shaped with a first end 80 at the open end of the u-shape and a second end 90 at the closed end of the u-shape (see FIGS. 6 and 7). The second end 90 includes a primary member 100 and a secondary member 110, which extends from and is angled relative to the primary member 100. First and second legs 120, 130 of the u-shaped base member 20 are integrally formed with the primary member 100. In use, the first and second legs 120, 130 extend around a bone graft to mitigate lateral shift of the graft and control subsidence of adjacent vertebrae as they set during fusion.

Subsidence is further controlled by the presence of the interface members 30 that extend from a portion of the base member 20. The interface members 30, as depicted in the present embodiment, can include a plurality of teeth extending from bottom surfaces of the primary member 100, the first leg 120, and the second leg 130. Accordingly, when coupled with the bone bodies, the interface members 30 extend from the base member 20 in a direction that is aligned with an elongate direction of the spine. The interface members 30 thus, are configured to provide a progressive penetration into the bone body over a period of time in a direction aligned with the elongate direction of the spine. It is to be appreciated, however, that any suitable configuration of interface members can be provided at any suitable location on the base member that interfaces with a surface of the bone body.

The interface members can include teeth, knife-edges, spikes, posts, pegs, and the like, including any combination thereof. The configuration of the interface members includes interlocking external features that impact a subsidence profile, which is a relationship between an applied load and an amount of settling the interbody device 10 experiences when secured to the bone bodies. Or in other words, the subsidence profile is a relationship between a depth of subsidence of the interface members and a force required to achieve the depth of subsidence. When first implanted, the interface members 30 will rest on top of the bone surface. When load is applied to the interbody device 10, the interface members 30 will penetrate, or subside, into the bone in a controlled manner. The interface members can readily dig into the bone initially and then slow down as more of the tooth cross section embeds. Different interface member configurations provide different controlled subsidence profiles. The density of the bone body also impacts the subsidence profile. For example, in a lower density bone body representation, such as 15 pcf foam, the interface members can penetrate the bone body by about 1 mm using between about 50-100 N of force and by about 2 mm using between about 150-250 N of force. In a medium density bone body, such as 20 pcf, the interface members can penetrate the bone body by about 1 mm using between about 100-200 N of force and by about 2 mm using between about 400-900 N of force. In a higher density bone body, such as 40 pcf, the interface members can penetrate the bone body by about 1 mm using between about 100-500 N of force and by about 2 mm using between about 1000-2250 N of force. The amount of force needed for displacement and the rate of penetration of the interface members into the bone body depends, in part, upon the configuration of the interface members. It should be noted that all of the pcf densities refer to polyurethane foam (which is referenced to ASTM standards) that is used as a bone analog for test purposes. The tests were also conducted using a straight test "blade" that was 40 mm long, not an actual implant.

Figure 4:
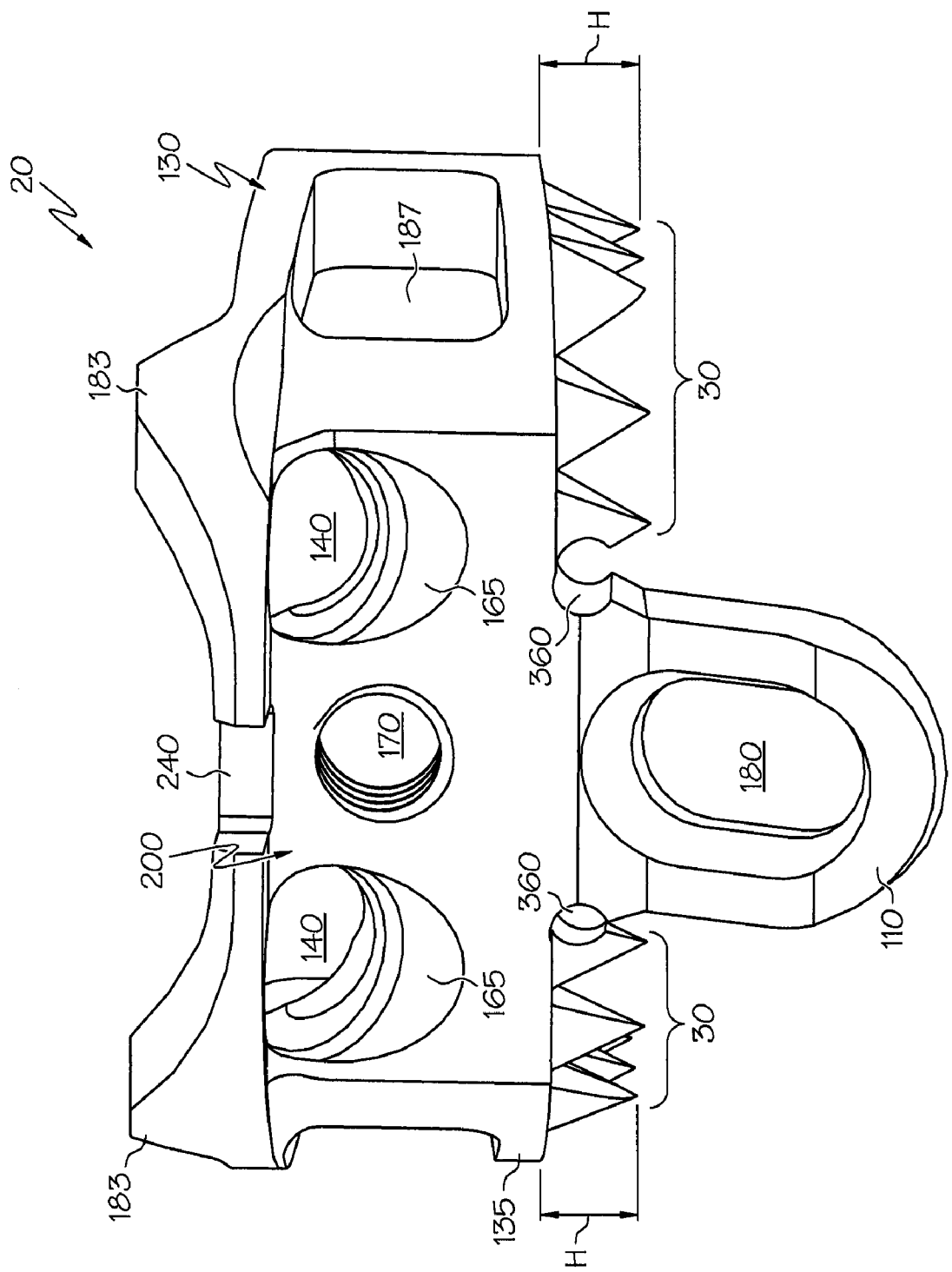
FIG. 4 is a front perspective view of a base member of an interbody device in accordance with an aspect of the present invention.
Figure 19:
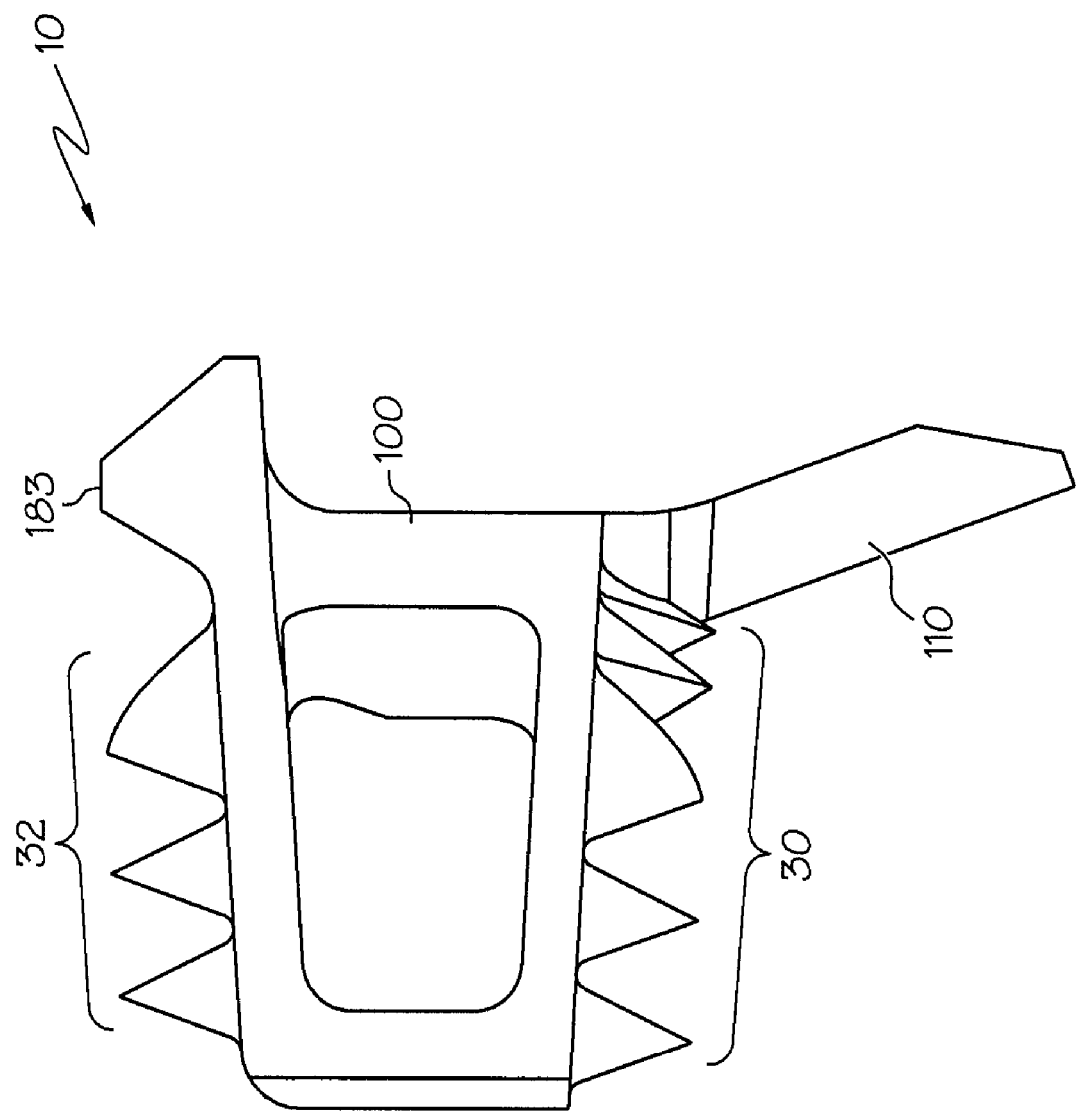
FIG. 19 is a side view of a base member of an interbody device in accordance with an aspect of the present invention.

The height (H) of the interface members 30 determines a depth of penetration into the bone body (see FIG. 4). Generally, when the interbody device 10 has subsided to a point where the interface members are fully embedded in the bone, the applied load will be distributed across the entire surface of the interbody device 10 and subsidence resistance will greatly increase. Typically, the screw will be at the end of the slot. Thus, the height (H) of the interface members can control an amount of subsidence that the interbody device 10 will permit. The interface members 30 can be of any height or combination of heights. Thus, if a plurality of interface members 30 extend from a surface of the base member, each interface member 30 can be of equal heights or substantially taller or shorter than other interface members. FIG. 19, as described in more detail below, illustrates that the interface members 30, 32 can extend from the top or bottom surfaces of the base member. The interface members 30, 32 can be of equal height or substantially dissimilar heights depending on the amount of subsidence resistance that is desired.

In addition to the height (H) of the interface members 30, the shape of the interface members 30 also affects subsidence of the interbody device 10. The shape of the interface members 30 controls a shape of the subsidence profile; and therefore, affects the load shared with the graft material. For instance, if the interface members 30 were limited to a few sharply pointed spikes, subsidence would occur substantially immediately and the interbody device 10 would rapidly seat in the bone to the fullest extent under low force. In this instance, any graft material would be immediately and highly loaded. Such immediate subsidence is not desirable because the joint space could narrow and cause nerve root or spinal cord compression. Also, the graft would be overloaded, inhibiting fusion. However, some subsidence is needed to load the graft and ensure fusion. Accordingly, by configuring the interface members 30 to have a broadly shaped portion, the interbody device 10 has increased resistance to subsidence as the interface members 30 penetrate into the bone body; and the graft material is gradually loaded as the device subsides. For instance, turning to FIG. 7, each tooth 30 is shaped with a substantially broad base, the base being defined by a length (L) and width (W) of each tooth. The substantially broad base of each tooth facilitates controlled subsidence of the interbody device 10. For instance, the as the tooth becomes wider in cross section, the penetration of the tooth into the bone body will become slower.

Once the interface members 30 have fully penetrated the bone, the surface area of the base member 20 is of an area large enough to resist further subsidence of the interbody device 10. To increase subsidence resistance, at an interface between the a plurality of teeth 30 and the bottom surfaces of the primary member 100 and the first and second legs 120, 130, a shelf-like area 135 is created. The shelf-like area 135 provides an extended surface area to contact the bone material, thereby increasing subsidence resistance once the interface members 30 have fully subsided. As mentioned, the screw will typically be at the end of the slot.

Figure 5:
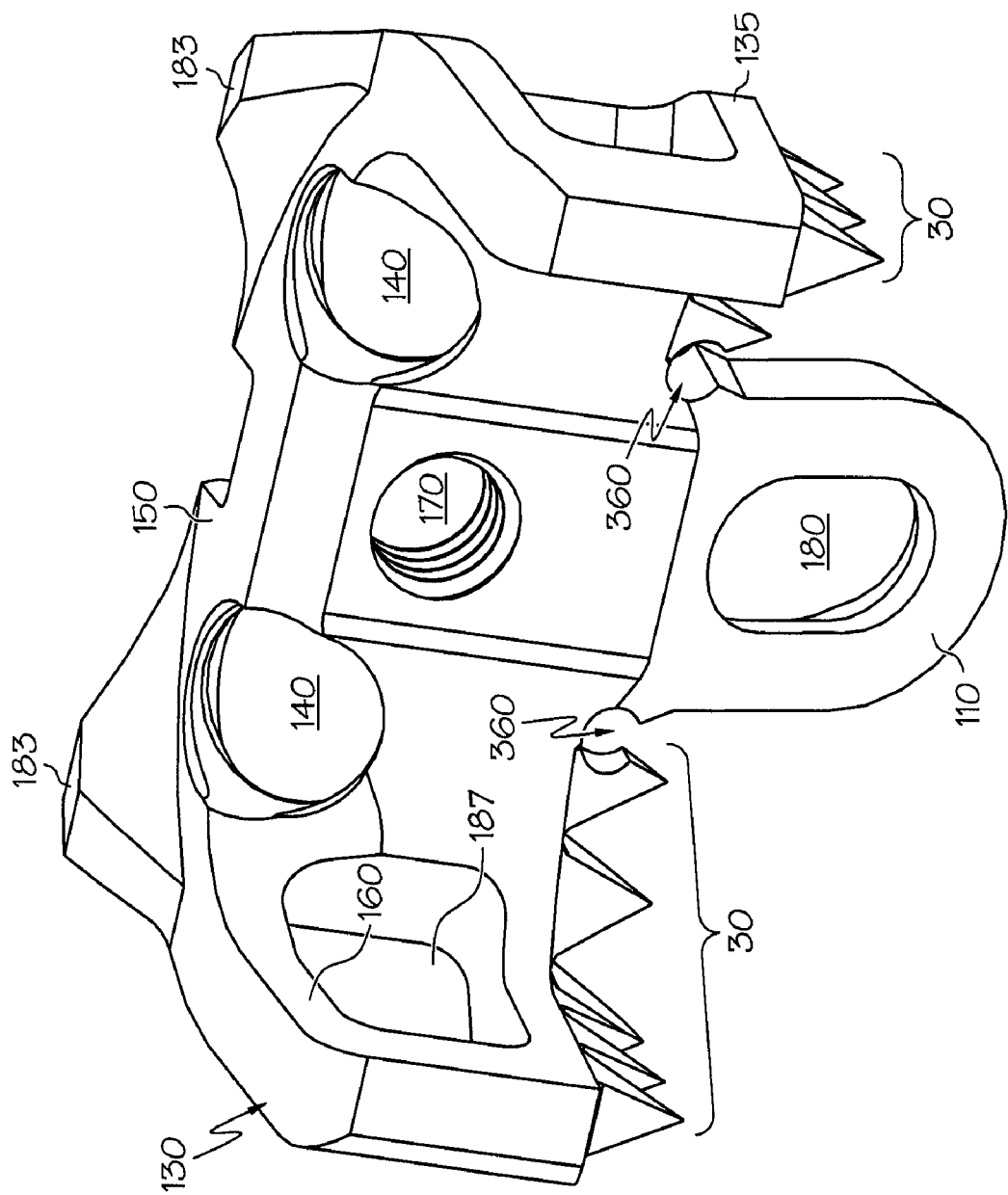
FIG. 5 is a back perspective view of a base member of an interbody device in accordance with an aspect of the present invention.
Figure 6:
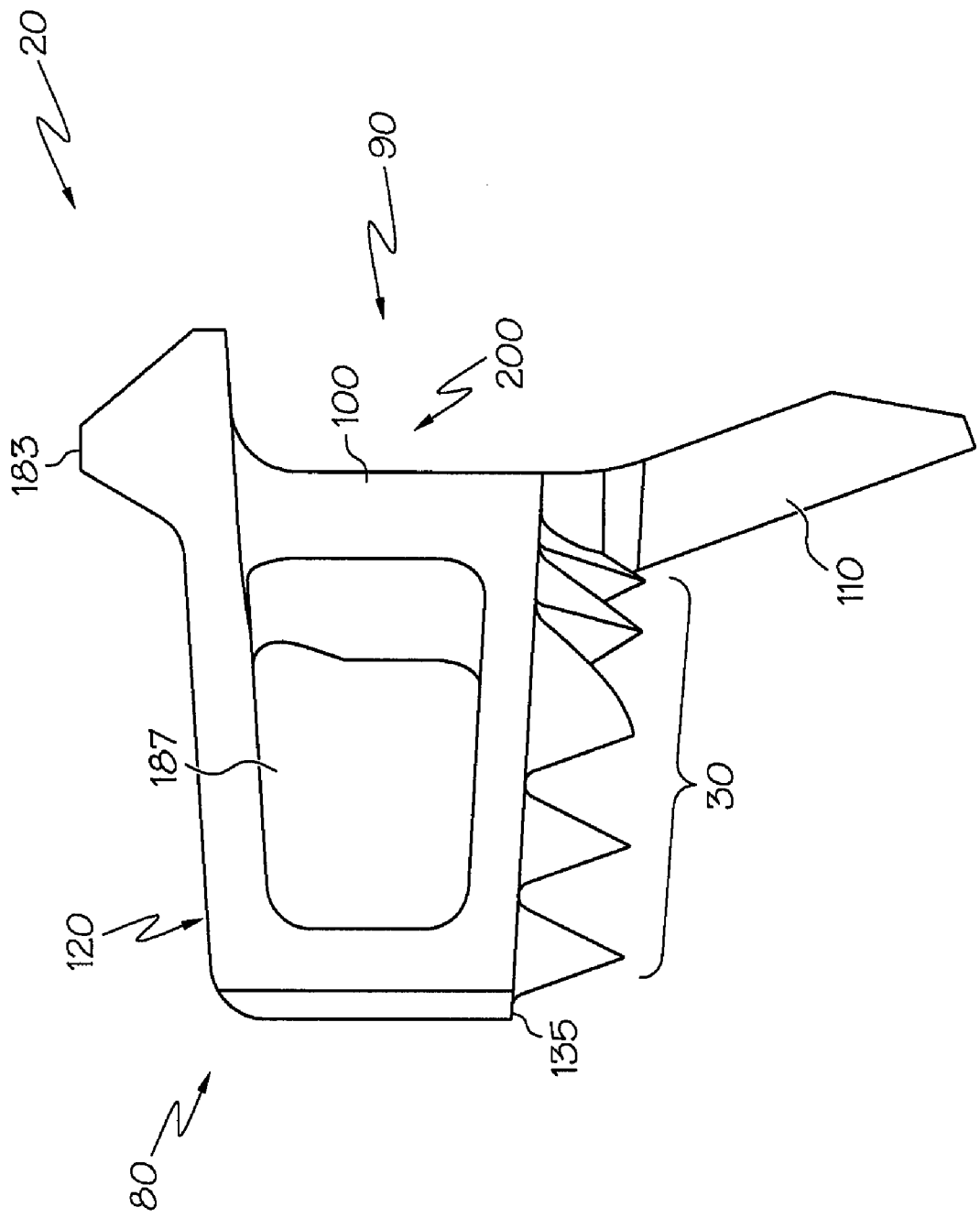
FIG. 6 is a side view of a base member of an interbody device in accordance with an aspect of the present invention.
Figure 7:
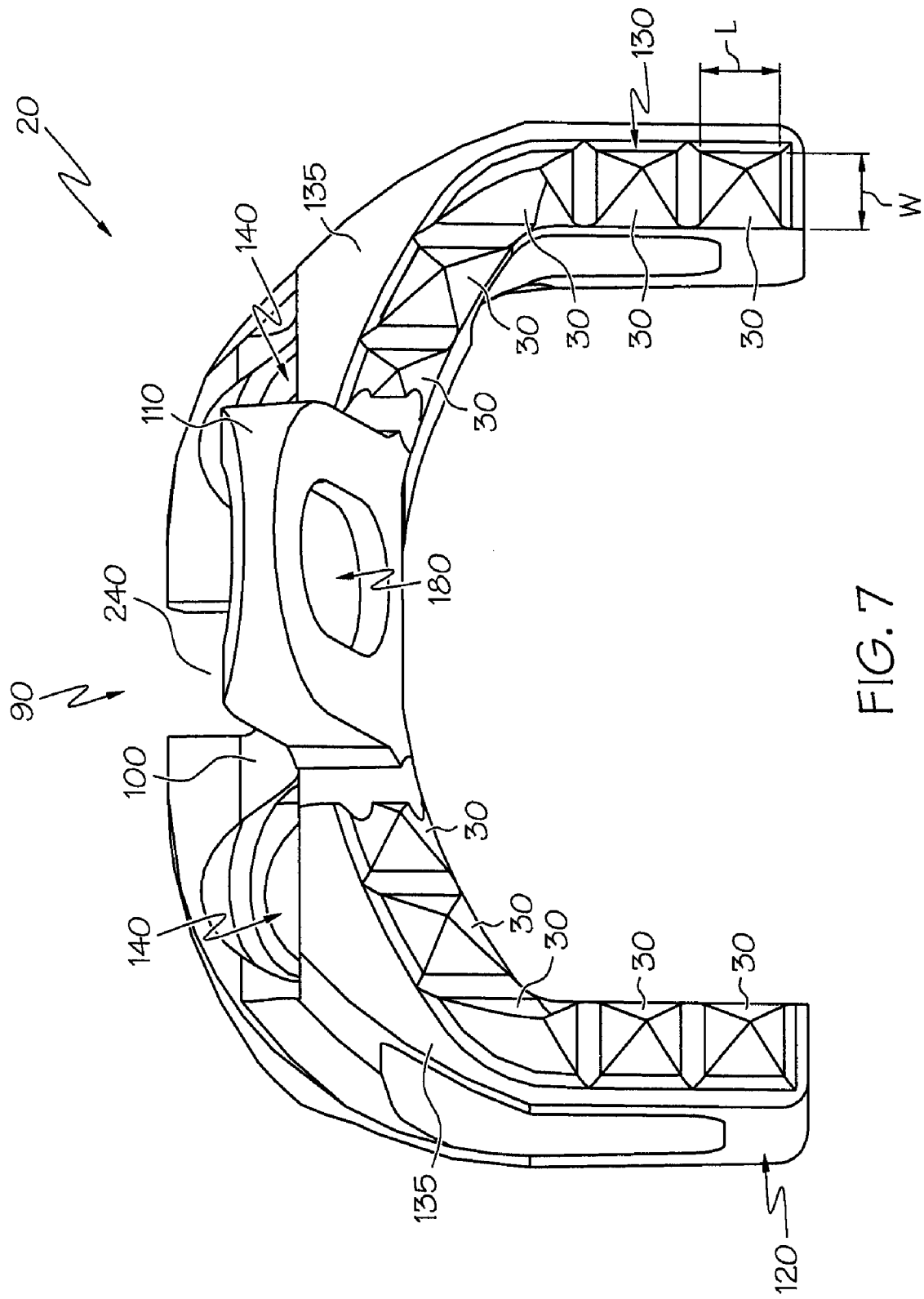
FIG. 7 is a bottom perspective view of a base member of an interbody device in accordance with an aspect of the present invention.

Turning back to the primary and secondary members 100, 110 of the base member 20, the secondary member 110 has a front surface that is generally continuous with a front surface of the primary member 100, as illustrated in FIG. 4 and a back surface that is generally continuous with a back surface of the primary member 100, as illustrated in FIG. 5. FIG. 6 illustrates the angular relationship between the primary and secondary members 100, 110. The primary member 100 and secondary member 110 are arranged relative to each other so that their front surfaces form an angle greater than 90° and less than 180°, preferably from 110° to about 160°. As will become apparent, the angle at which the primary and secondary members 100, 110 are joined is provided so that bone screws can be introduced through the base member 20 at desired angles, as discussed further below. Accordingly, the base member 20 can be designed in any other manner that permits the bone screws to be introduced therethrough at the desired angles.

The primary member 100 includes at least one, and preferably two (as shown in the depicted embodiment) first bone screw holes 140 extending therethrough, each configured to receive a corresponding bone screw. The first bone screw holes 140 in the primary member 110 are configured such that bone screws extend through the holes 140 at an angle, as illustrated in FIG. 3. For example, the first bone screw holes 140 can extend through a corner that joins a top surface 150 of the base member 20 to a back surface 160 of the base member 20, as best shown in FIG. 5. As a result, each bone screw extending through the first bone screw holes 140 can enter the bone body at an angle, as discussed further below. Each of the first bone screw holes 140 is sufficiently large to allow a portion of a respective bone screw to pass therethrough but not large enough to allow a retaining portion of the bone screw through, such as the head of the bone screw. Further, each of the first bone screw holes 140 has a seat 165 on which the retaining portion of a respective bone screw rests. Each seat 165 has a generally concave spherical shape and the surface of the retaining portion of the bone fastener in contact with the seat 165 has a complementary convex spherical configuration. Consequently, the bone screws are free to pivot on the seats 165. The primary member 100 also includes a threaded hole 170 for receiving the restraining member fastener 70.

The secondary member 110 includes a second bone screw hole 180 in the form of an elongated slot for receiving a bone screw. The bone screw is introduced into the second bone screw hole 180 and into a second bone body. The second bone screw hole 180 is configured such that a bone screw can slide and rotate within the slot relative to the base member 20 and generally toward the primary member 100. Thus, in use, as two adjacent bone bodies, to which the base member 20 is fixed, collapse or settle and move toward each other, the bone screw contained within the second bone screw hole 180 will slide within the slot and move with the bone body into which it extends in a direction toward the primary member 100 and the other bone body.

At least one and preferably two projections 183 extend upwardly from the top surface 150 of the base member 20. The projections 183 contact a surface of the bone bodies to provide a stop when inserting the base member 20 between the bone bodies. The base member 20 also includes holes 187 provided through each of the first and second legs 120, 130. The holes 187 facilitate visualization of the fusion mass on x-rays and bone growth therethrough when the interbody device 10 is positioned between two bone bodies.

The base member 20 may be made of any suitable material, and is preferably made from titanium or a titanium alloy. The thickness of the base member 20 is not critical, and preferably ranges from about 1 mm to about 2 mm, and more preferably is about 1.6 mm. The height of the base member 20 will depend on the needs of the particular patient.

Figure 8:
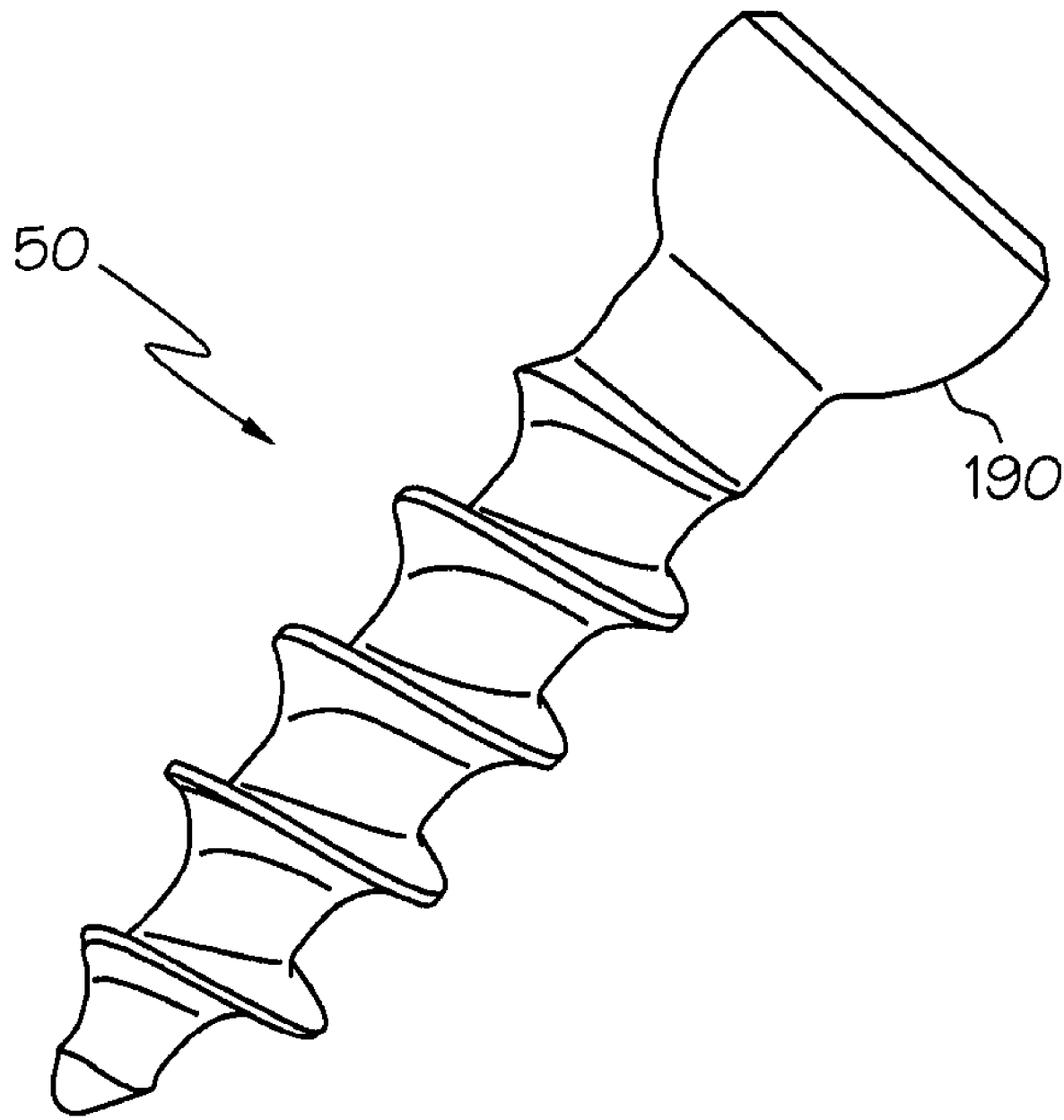
FIG. 8 is a perspective view of a bone screw of an interbody device in accordance with an aspect of the present invention.

Turning now to FIG. 8, the bone fastener 50 is illustrated in further detail in accordance with an aspect of the present invention. The bone fastener 50 can comprise a bone screw, a plurality of which is used for securing the interbody device 10 to the bone bodies. The bone fasteners 50 can be made of any suitable material, and are preferably made of the same material as the base member 20, such as titanium or a titanium alloy. The bone fasteners 50 can all have the same shape, such as that shown in FIGS. 1-3. In the depicted example, the bone fasteners each have a radiused head 190. As used herein, the term "radiused head" means that the lower portion of the bone screw head, i.e., the portion that is nearest the shank, is generally rounded, to thereby permit the bone screws to toggle within their respective holes 140 and 180. The bone fasteners 50 can have any other suitable shape that permits them to cooperate with the first and second bone screw holes 140 and 180 or the elongated slots of FIGS. 17 through 22.

The bone fasteners 50 can be undersized to permit the bone fastener to slide in a bone screw hole. For instance, the bone fastener may be positioned in a bone body such that the retaining portion, such as the head, does not rest on the seat of the hole and the portion of the bone fastener extending into a bone body is not fully embedded. In this case, it is desirable that the portion of the bone fastener extending into a bone body is substantially small. Reducing the non-embedded portion of the bone screw tends to ensure that the retaining potion of the bone fastener does not protrude outward from the hole in a manner that renders it difficult to position a retaining means over the bone fastener. To permit the bone fastener 50 to slide in the hole, the diameter of the portion extending into a bone body is substantially less than the diameter of the hole. The bone fastener 50 can be positioned at one edge of the hole so that the bone fastener may slide within the diameter of the hole until it becomes in contact with the opposite edge of the hole. The hole in this case functions as an elongated slot as described with regard to FIGS. 17 through 22. In this regard, the hole has a small elongation length that allows the bone fastener to slide. Thus, the length of travel is controlled by the difference of the respective diameters of the hole and the portion of the screw extending into a bone body. In other words, the more undersized the portion of the bone fastener that extends into a bone body, the more slide length that will be available.

Figure 9:
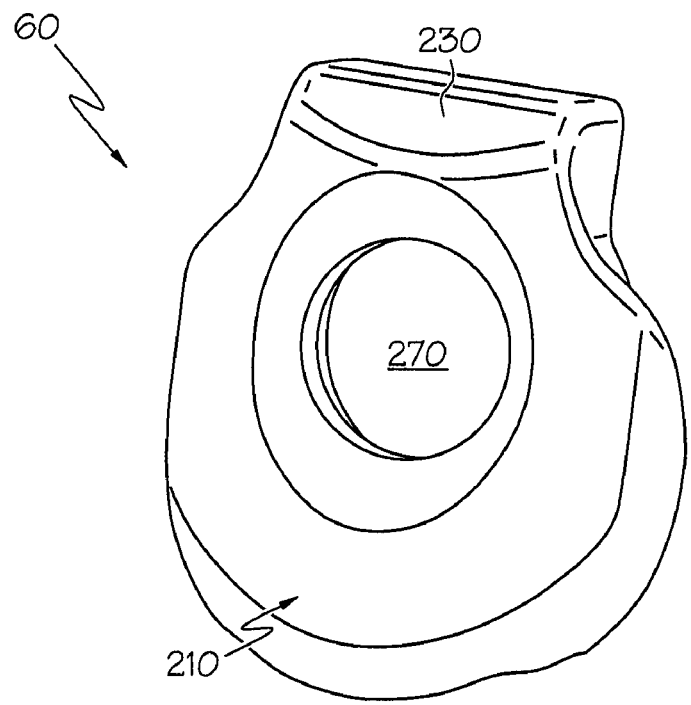
FIG. 9 is a front perspective view of a restraining member of an interbody device in accordance with an aspect of the present invention.
Figure 10:
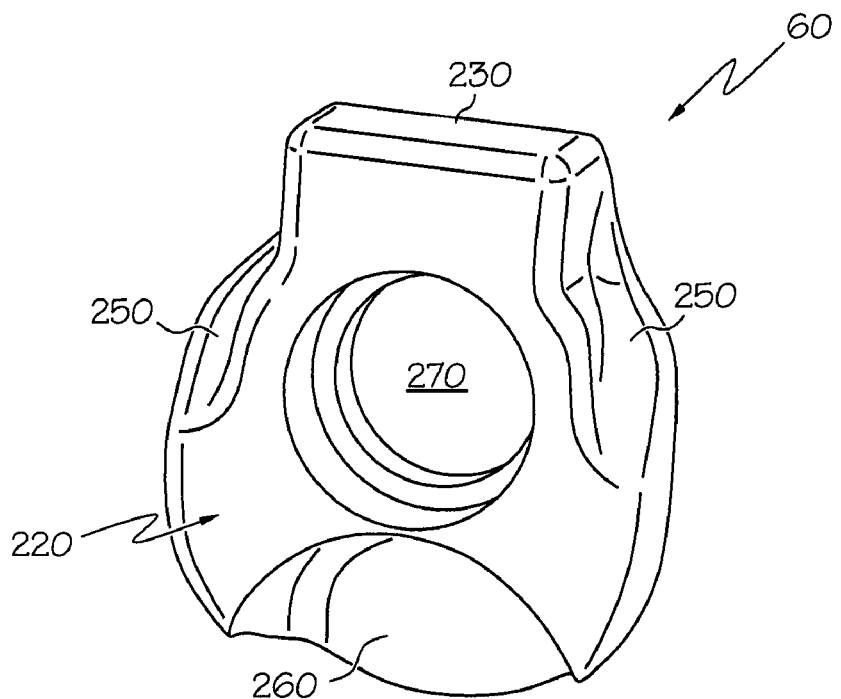
FIG. 10 is a back perspective view of a restraining member of an interbody device in accordance with an aspect of the present invention.

The bone fasteners are secured to the base member 20 via restraining means. As stated above, the restraining means can include a restraining plate 60, an example of which is illustrated in FIGS. 9 and 10 in accordance with an aspect of the present invention. The restraining plate 60 is configured to correspond with a recessed region 200 of the base member 20 of the interbody device 10 (see FIGS. 4 and 6). More specifically, the restraining plate 60 includes a generally rounded front side 210 and a generally flat back side 220. The restraining plate 60 has a flange 230 formed in a top portion of the plate, the flange 230 being configured to fit within a corresponding groove 240 formed in the base member 20. The use of the recessed region 200 and the groove 240 in the base member 20 facilitates proper positioning of the restraining plate 60 on the base member 20. The thickness of the restraining plate 60 is not critical, but should generally be as thin as possible. Some example thicknesses are preferably in the range from about 0.5 mm to about 2 mm, more preferably from about 1 mm to about 1.5 mm.

Turning to FIG. 10, the restraining plate 60 includes a plurality of notches formed along the edges of its back surface 220. The notches include at least one generally rounded notch 250, preferably two, each of the generally rounded notches 250 configured to correspond with one of the bone screws 50. When the restraining plate 60 is fixed in place over the base member 20, the generally rounded notches 250 each cover a portion of a corresponding one of the bone screws 50. The notches 250 are generally rounded so as to permit the bone screws 50 to toggle within the first bone screw holes 40. The restraining plate 60 can also include a substantially U-shaped notch 260, which is curved outwardly towards the edge of the restraining plate 60. When the restraining plate 60 is fixed in place over the base member 20, the top of the bone screw 50 positioned within the second bone screw hole 180 sits within the U-shaped notch 260. Thus, a top of the bone screw 50 is covered by the top surface of the restraining plate 60. With this design, the bone screw 50 positioned within the second bone screw hole 180 is permitted to slide and toggle within the slot even when the restraining plate 60 is fixed over the bone screw 50.

The restraining plate 60 also includes an aperture 270 formed therethrough. The aperture 270 in the restraining plate 60 is aligned with a hole 170 in the primary member 110 of the base member 20, both of which can receive a restraining member fastener 70 for fixing the restraining plate 60 in place over the base member 20. The restraining member fastener 70 can be made of any suitable material well known in the art, preferably titanium or a titanium alloy. The restraining member fastener 70 can be a screw, such as a hexagonal screw that can be turned with a hexagonal driver. Other types of fasteners can also be used, as well as any other suitable mechanism for fixing the restraining plate 60 to the base member 20. In one embodiment, the mechanism does not permanently fix the restraining plate 60 to the base member 20 so that device 10 can be removed if desired. The precise mechanism by which the restraining plate 60 is fixed to the base member 20 is not critical to the invention.

In one embodiment the restraining plate 60 functions to prevent the bone screws 50 from backing out of the bone bodies once the bone screws 50 are screwed in. That is, the notches 250 and the U-shaped notch 260 cover the bone screws 50 extending through the base member 20 such that the top surface of the restraining plate 60 does not come into contact with the bone screws 50. When the restraining plate 60 is fixed in place over the bone screws 50, the top surface of the restraining plate 60 does not interfere or contact the bone screws 50 as they toggle or slide in the bone screw hole 40 or slot 180. The top surface of the restraining plate 60 contacts or restricts the movement of the bone screws when the bone screws 50 back out or loosen from the bone bodies. Thus, during normal use of the implanted device 10, the restraining plate 60 does not tend to impede the movement of the bone screws 50.

In another embodiment, which is not shown, the restraining plate 60 can have a top surface and/or notches that contact or interface with the head of at least one bone screw 50. The interface between the top surface or notch of the restraining plate 60 and a corresponding bone screw 50 prevents the bone screw 50 from backing out of the bone body and tends to exert force on the bone screw 50 so as to control the movement of the screw 50 in the hole 140 or slot 180 of the base member 20. Depending on the surface dimensions of the restraining plate 60 and the shape of the bone screw 50 head, the interface between the plate 60 and a bone screw 50 can control the amount of toggle or slide of a bone screw 50. For example, the restraining plate 60 can include a notch configured to match the rounded head of a corresponding bone screw 50, wherein the notch also has a stop plate or restraining surface. When the bone screw 50 toggles in the slot of the base member 20, the head rotates along the interface with the corresponding notch in the restraining plate 60 until the head of the bone screw 50 reaches the stop plate. In this regard, the top surface or notch of the restraining plate 60 can be designed so the interface with a bone screw 50 can be used to control the amount of movement or resistance a bone screw 50 is subject to in order to create resistance to movement thereof.

In yet another embodiment, which is not shown, the surface portions of the restraining plate 60 that interface with the bone screws 50 can be substantially angled such that the interface portions of the restraining plate 60 are flush with the top surface of the bone screw 50 heads. That is, the surface portions of the restraining plate 60 that interface with the top surface of the bone screw 50 heads rest flat against the heads and restrain the bone screws from toggling or rotating in the hole or slot the bone screws 50 extend through. In the case which the bone screw 50 extends through a slot in the interbody device 10, the restraining plate 60 can also include a stop plate that extends from the surface of the restraining plate 60 into the slot. When the bone screw 50 is at one end of the slot, the stop plate extending downward into the slot can prevent the bone screw 50 from sliding along the entire elongation length of the slot. The stop plate can be positioned at any point along the elongation length of the slot so that the distance the bone screw 50 slides in the slot can be controlled. Subsidence resistance can also be controlled in part by the positioning of the stop plate in the slot. For example, if the stop plate is positioned near the opposite end of the slot from the end where the bone screw 50 is located, the bone screw 50 can slide along substantially the entire elongation length of the slot and thus subsidence resistance may be decreased. On the other hand, if the stop plate is positioned near the location of the bone screw 50 in the slot, the distance the bone screw 50 can slide along the elongation length of the slot is decreased and subsidence resistance may be increased.

Figure 23:
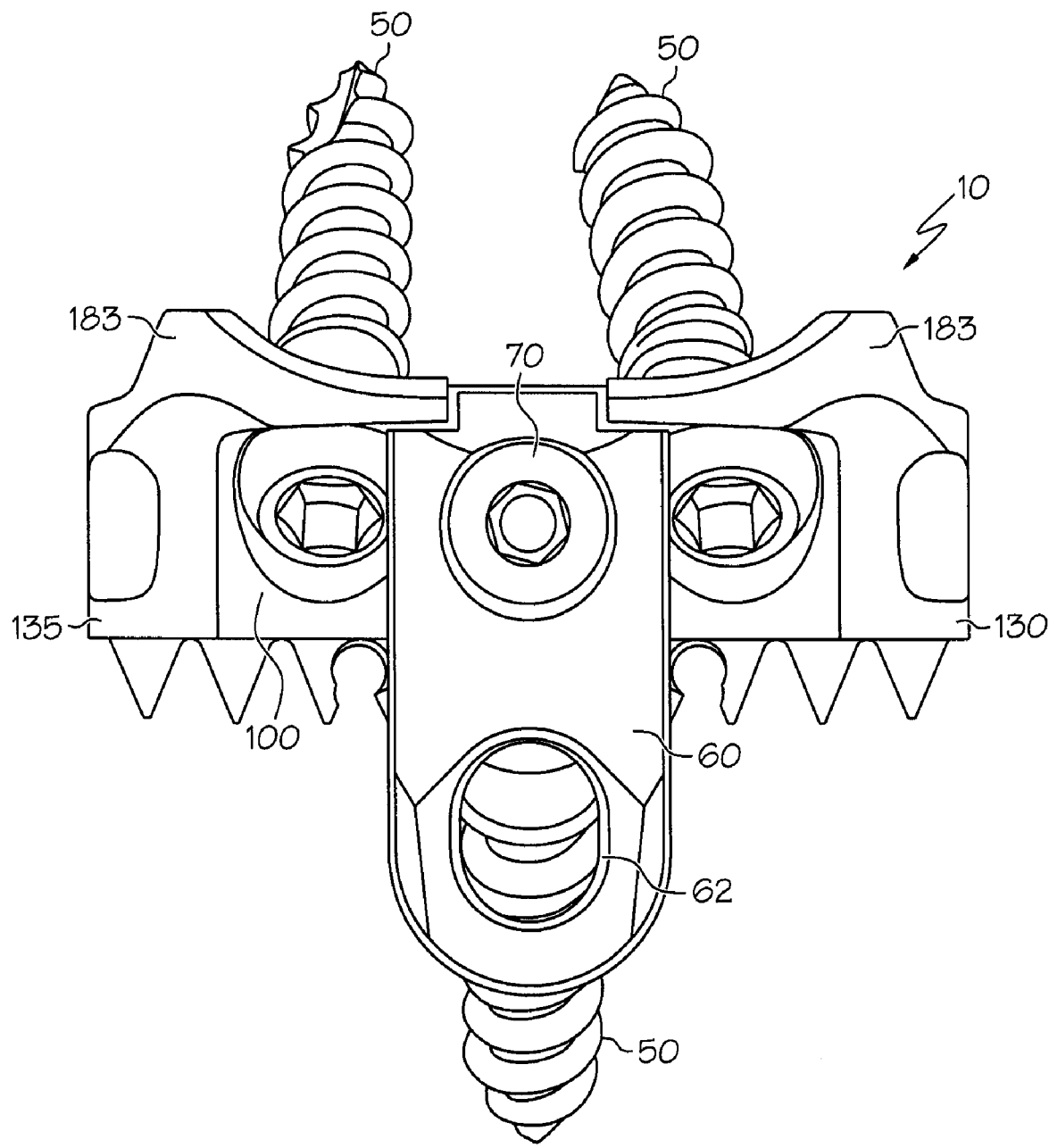
FIG. 23 is a front perspective view of an interbody device in accordance with an aspect of the present invention.
Figure 24:
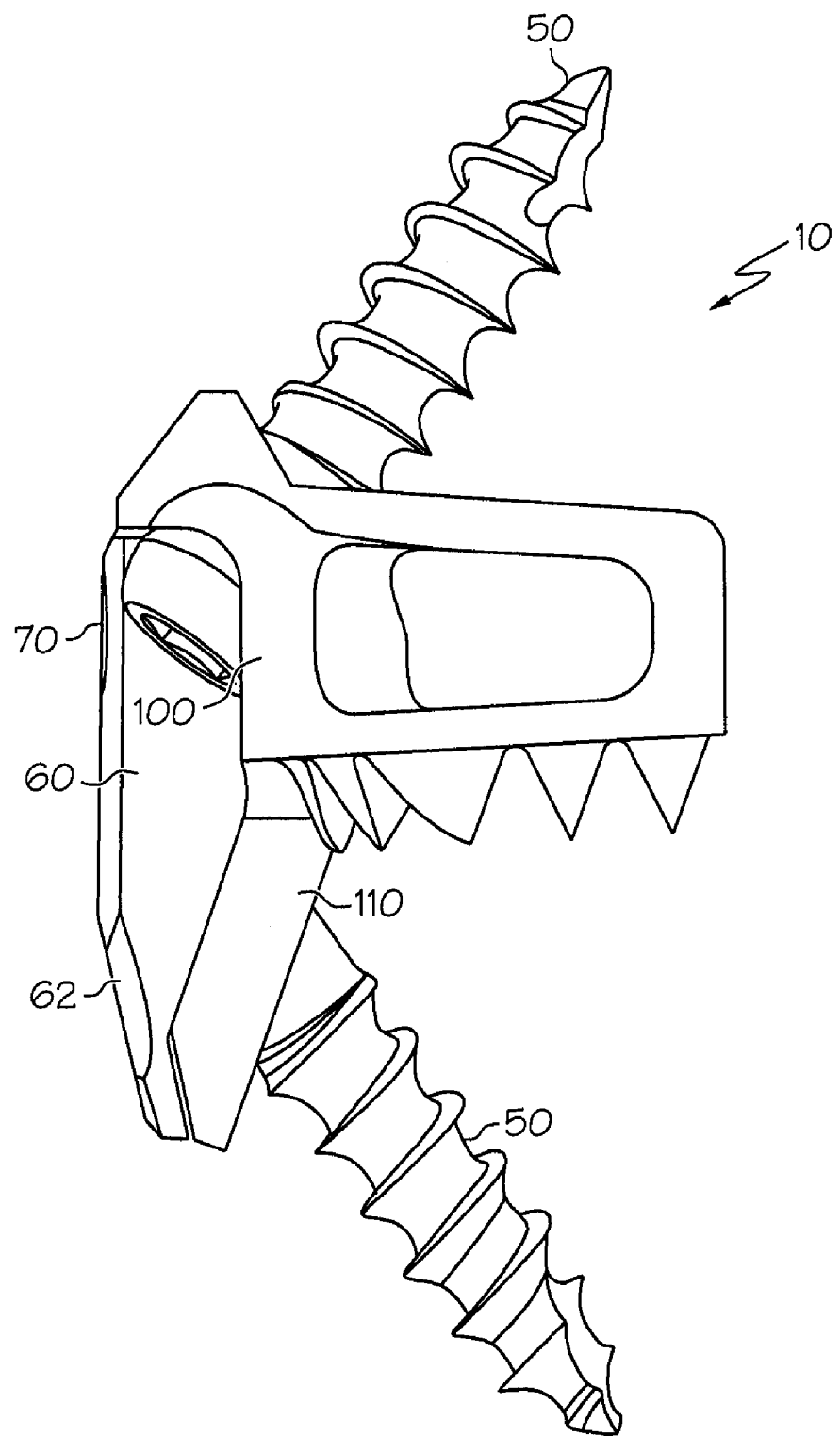
FIG. 24 is a side perspective view of another interbody device in accordance with an aspect of the present invention.

FIGS. 23 and 24 illustrate another embodiment of a restraining plate 60 that can be used with the interbody device 10. The restraining plate 60 of FIGS. 23 and 24 is attached or fixed to the interbody device 10 by means of a screw 70. The restraining plate 60 covers a portion of the bone screw 50 heads passing through the primary member 100 and extends downward over the bone screw 50 passing through the secondary member 110. The bone screw 50 passing through the secondary member 110 is substantially covered by the restraining plate 60. As shown in FIG. 23, the restraining plate 60 can have an open area 62 that exposes the bone screw 50 passing through the secondary member 110. The open area 62 of the restraining plate 60 allows the bone screw 50 to more easily slide or toggle in the aperture it passes through. As shown in FIG. 24, the restraining plate 60 rests flush against the interbody device 10 on the surfaces of the primary member 100 and secondary member 110. The shape or contour of the restraining plate 60 allows for a custom fit with the interbody device 10 such that the front portion of the interbody device 10 is substantially flat.

Additionally, it is to be appreciated that any other suitable bone screw restraining means can be used in connection with the present invention. For example, the bone screw restraining means can comprise multiple restraining plates that cover different bone screws. Alternatively, the bone screw restraining means can comprise one or more screws with heads that overlap at least a portion of one or more bone screws to thereby prevent the bone screws from backing out.

Figure 11:
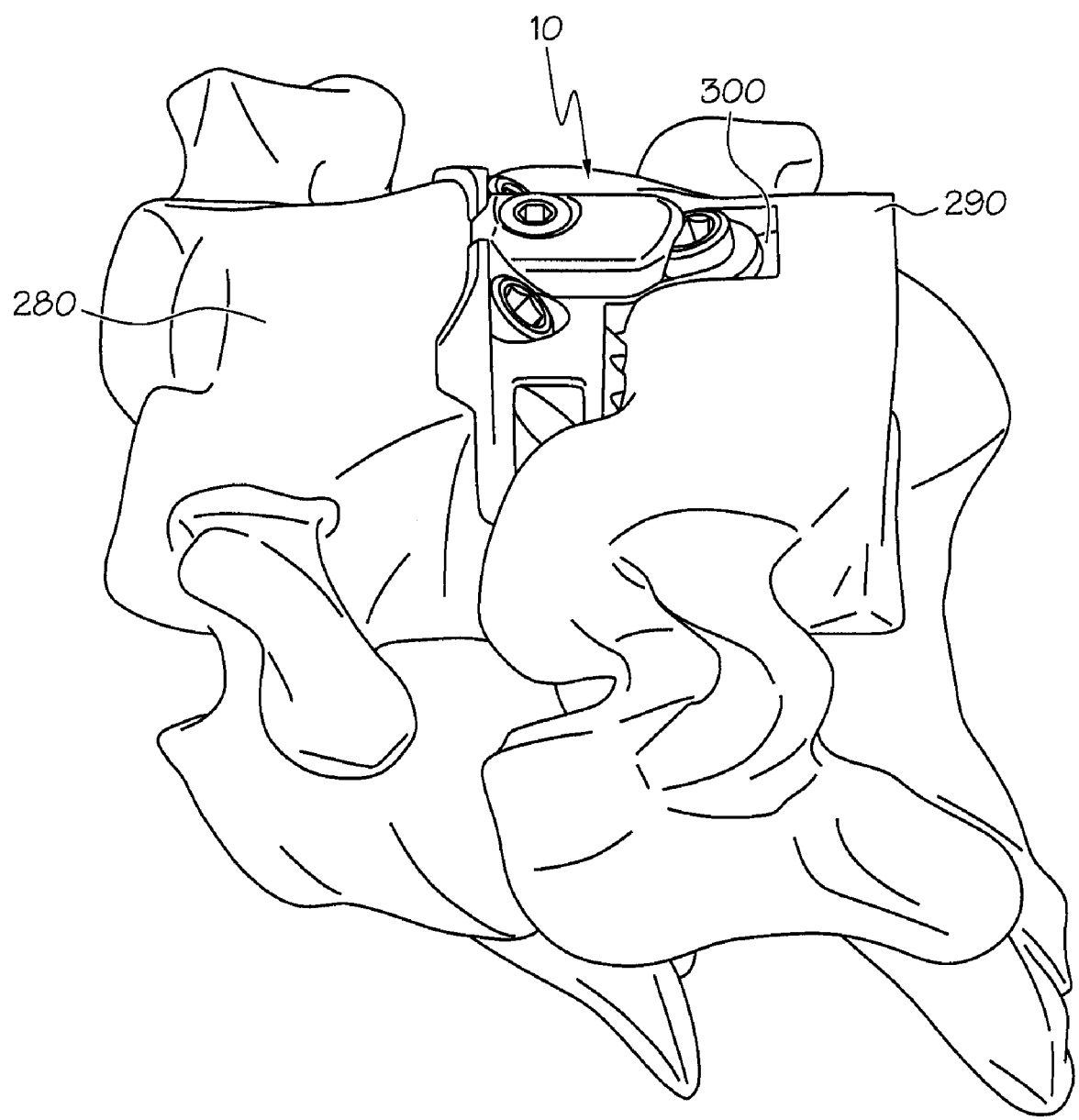
FIG. 11 is a side perspective view of an interbody device positioned between two bone bodies in accordance with an aspect of the present invention.
Figure 12:
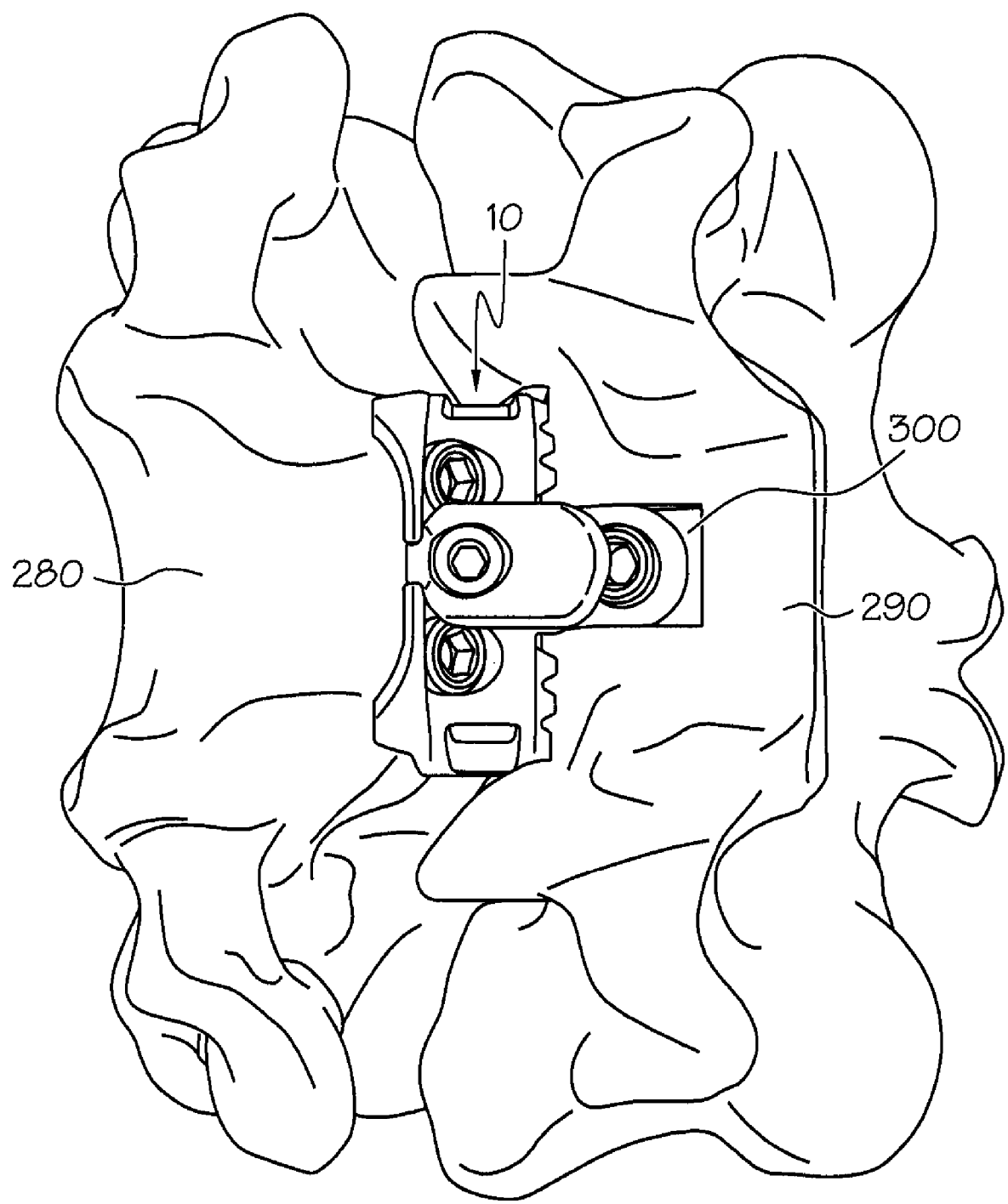
FIG. 12 is a top perspective view of an interbody device positioned between two bone bodies in accordance with an aspect of the present invention.

FIGS. 11 and 12 illustrate the interbody device 10 secured between two bone bodies 280 and 290 in accordance with an aspect of the present invention. The bone bodies 280 and 290 can be two adjacent vertebrae and the interbody device 10 can be mounted to the vertebrae with a bone graft (not shown) between the vertebrae. More specifically, the base member 20 of the device 10 is mounted to the vertebrae by attaching the bone fasteners 50, which are located in bone screw holes 140, to one of the cervical vertebrae 280 to be stabilized and the bone fastener 50, which is located in slot 180, to the other of the cervical vertebrae 290 to be stabilized. The base member 20 is positioned such that the first and second legs 120, 130 lie generally opposite the bone graft between the two vertebrae. The bone fasteners 50 are driven into the vertebrae 280, 290 sufficiently so that the convex spherical configuration of the bone fasteners 50 bear against the seats 165 of the bone screw holes 140 and secure the base member 20 against anterior surfaces of the two cervical vertebrae 280, 290. More specifically, the bone fasteners 50 provided through the bone screw holes 140 are driven through an end surface of bone body 280; and the bone fastener 50 provided through the slot 180 is driven through a top surface of bone body 290.

To provide an enhanced fit, a few millimeters of bone can be trimmed or otherwise removed from a lip osteophyte of the second vertebral body 290 at an angle corresponding to the angle of the secondary member 110 of the base member 20. The trimmed surface provides a substantially flat surface 300 for anchoring the bone screw 50 into the lip osteophyte of the second vertebral body 290. The surface also accommodates sliding of the tab as the teeth subside into the second vertebral body 290.

The angles of the bone screws 50 relative to the bone surfaces of the vertebral bodies 280, 290 are important. The lip osteophyte is the strongest part of the bone, and thus angling the bone screws 50 through the lip osteophyte increases the ability of the base member 20 to stay anchored to the vertebral bodies 280, 290. Moreover, by being angled, each bone screw 50 is positioned along an angle of rotation of a corresponding vertebral body 280, 290 as well as an angle of settling of the vertebral body 280, 290. This places each screw 50 in a protected position against motion of the spinal column. As a result, significant shear forces are not exerted on the screws 50 as the vertebral bodies 280, 290 rotate and settle.

Figure 13:
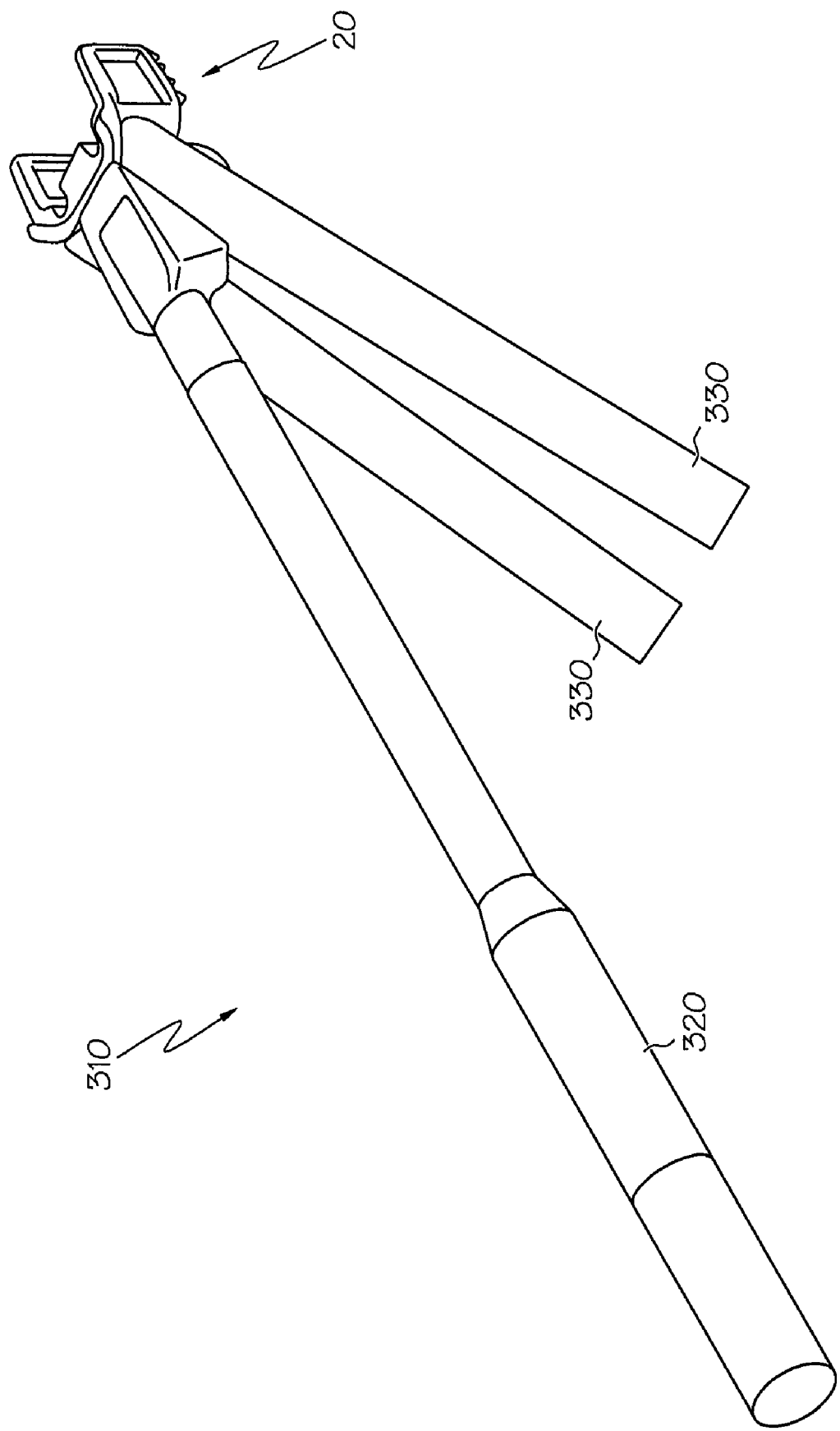
FIG. 13 is a perspective view of a guide tube system for inserting bone screws into a base member of an interbody device in accordance with an aspect of the present invention.

A first guide tool 310 as illustrated in FIG. 13 can be provided to allow a surgeon to hold and position the base member 20 against the bone, and to accurately drill into the bone. The guide tool 310 includes a handle 320 for holding and manipulating a position of the guide tool 310. A projection (not shown) extends from a base portion of the guide tool 310 and is configured to engage hole 170 in the primary member 100 of the base 20 to hold the guide tool 310 in position. When the handle 320 is properly engaged with the base member 20, a pair of guide tubes 330 is properly lined up with corresponding bone screw holes 140. The surgeon then inserts a drill or center punch (not shown) through one of the guide tubes 330 to drill a hole in the bone, through the screw hole 140. Then, after removing the drill, the surgeon inserts a bone screw 50 held at the end of a suitable driver (not shown) through the guide tube 330, and screws it into the bone. The process is repeated until the desired number of screws are placed, leaving the base member secured to the bone via the first bone screw holes 140. Or, since the first guide tool 310 includes two guide tubes 330, the bone screws 50 can be inserted at substantially the same time.

Figure 14:
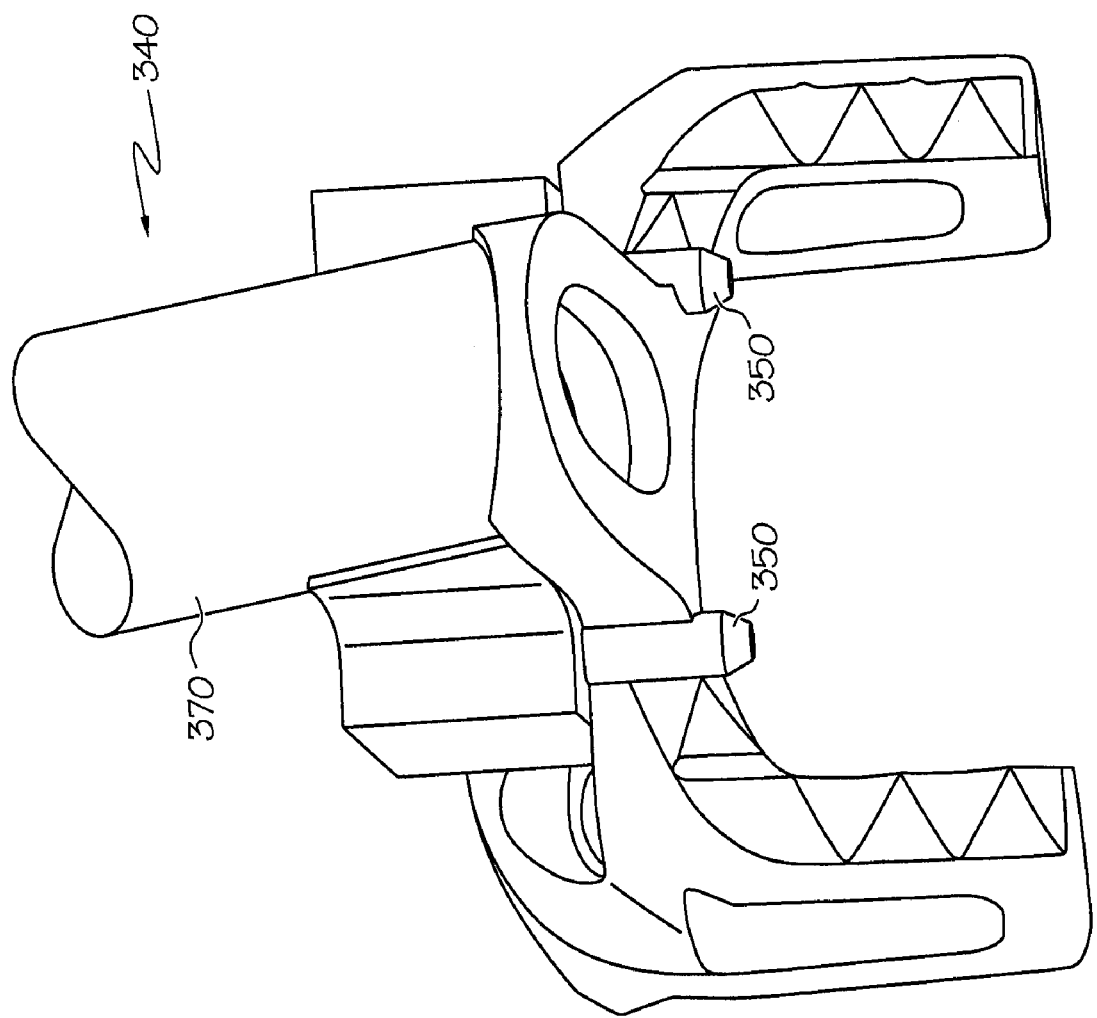
FIG. 14 is a bottom perspective view of another guide tube system for inserting a bone screw into a base member of an interbody device in accordance with an aspect of the present invention.

A second guide tool 340 is illustrated in FIG. 14 is also provided to allow a surgeon to hold and position the base member 20 against the bone, and to accurately drill into the bone. More specifically, the second guide tool 340 is employed to drill a bone screw 50 into the bone slot 180. The second guide tool 340 includes two substantially round projections 350 that engage corresponding notches 360 provided between the secondary member 110 of the base 20 and an adjacent interface member 30 provided on each side of the secondary member 110 (see FIGS. 4 and 5) to hold the second guide tool 340 in position. As above, the surgeon then inserts a drill (not shown) through a guide tube 370 to drill a hole in the bone, through the screw slot 180. Then, after removing the drill, the surgeon inserts a bone screw 50 held at the end of a suitable driver (not shown) through the guide tube 370, and screws it into the bone. It should be noted that one function of the guide is to locate the screw at the end of the slot so the screw travel can match subsidence of the teeth. If for example the screw was placed in the center of the slot it would bottom out in the slot before the teeth had fully embedded.

In another embodiment, the bone screw 50 configured to pass through the apertures in the base member 20 can have pointed ends which comprise a cutting flute on the tip. The cutting flute at the tip of the bone screw 50 allows the screw to be self-drilling or self-tapping. Thus, the use of a bone screw 50 having a self-drilling or self-tapping tip makes the use of a drill or center punch optional.

Turning back to FIGS. 11 and 12, once the bone screws 50 are inserted into the bone screw holes 140 and the bone screw slot 180, the restraining plate 60 is placed over the base member and fixed in place to prevent the screws 50 from "backing out" of the screw holes 140, 180. The second bone screw 50 that extends through the bone screw slot 180 is nonetheless permitted to slide along the length of the slot 180, even when the restraining plate 60 is secured in place. Thus, second the bone screw 50 and the bone screw slot 180 cooperate to control any lateral or rotary movement of one vertebral body relative to an adjacent vertebral body during "settling" of the bone. Further, the angled orientation of the second member 110 provides the base member 20 with resilient properties, for example, enabling the base member 20 "flex" when one vertebra is rotated relative to an adjacent vertebrae.

shown in FIG. 12, the interbody device 10 of the present invention has a substantially low profile. Namely, the base member of the present invention is designed to have an outer periphery that coincides with or generally matches the outer diameter of the cortex. The top surface of the base sits at, and preferably below, the top surface of the vertebral bodies. As such, the interbody device 10 of the present invention does not have any parts that would significantly interfere with or irritate the trachea, esophagus, and/or other anatomic structures of the patient.

Another advantage of the interbody device 10 is that it is stackable. Frequently after a bone graft is inserted and a bone plate joined to the surrounding vertebral bodies, for example, C4 and C5, an adjacent disk, for example, between C5 and C6, subsequently deteriorates. With traditional bone plates, it would be necessary to remove the plate from C4-C5 before attaching a second bone plate to C5 and C6 because each plate covers a significant surface of the vertebral body. To remove a bone plate, it is necessary dissect scar tissue, which can have a negative impact on the patient. In contrast, the interbody device 10 of the present invention covers an insignificant portion of the top surfaces of the vertebral bodies to which it is attached, instead being located primarily between the vertebral bodies. As a result, multiple interbody devices can be introduced over adjacent bone grafts (i.e., between a common vertebral body) so that two interbody devices are attached to a common vertebral body without the bone plate systems contacting one another. Thus, subsequent procedures where new bone grafts are to be inserted do not require the removal of a pre-existing device prior to introduction of a new device. The depicted systems where the bone screws are provided in a generally triangular arrangement further enhance the stacking ability of the interbody devices of the invention.

Figure 15:
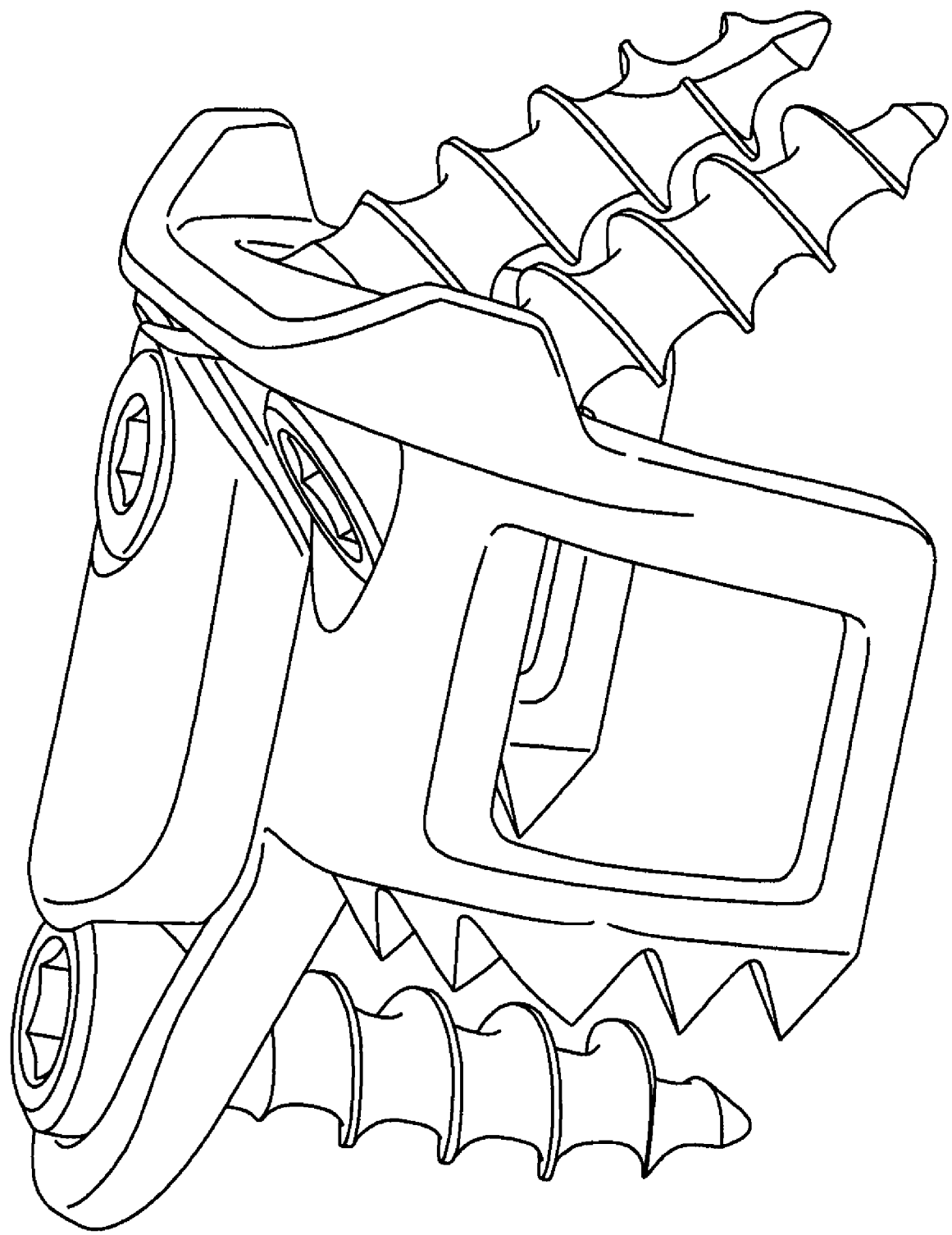
FIG. 15 is a side perspective view of another interbody device in accordance with an aspect of the present invention.
Figure 16:
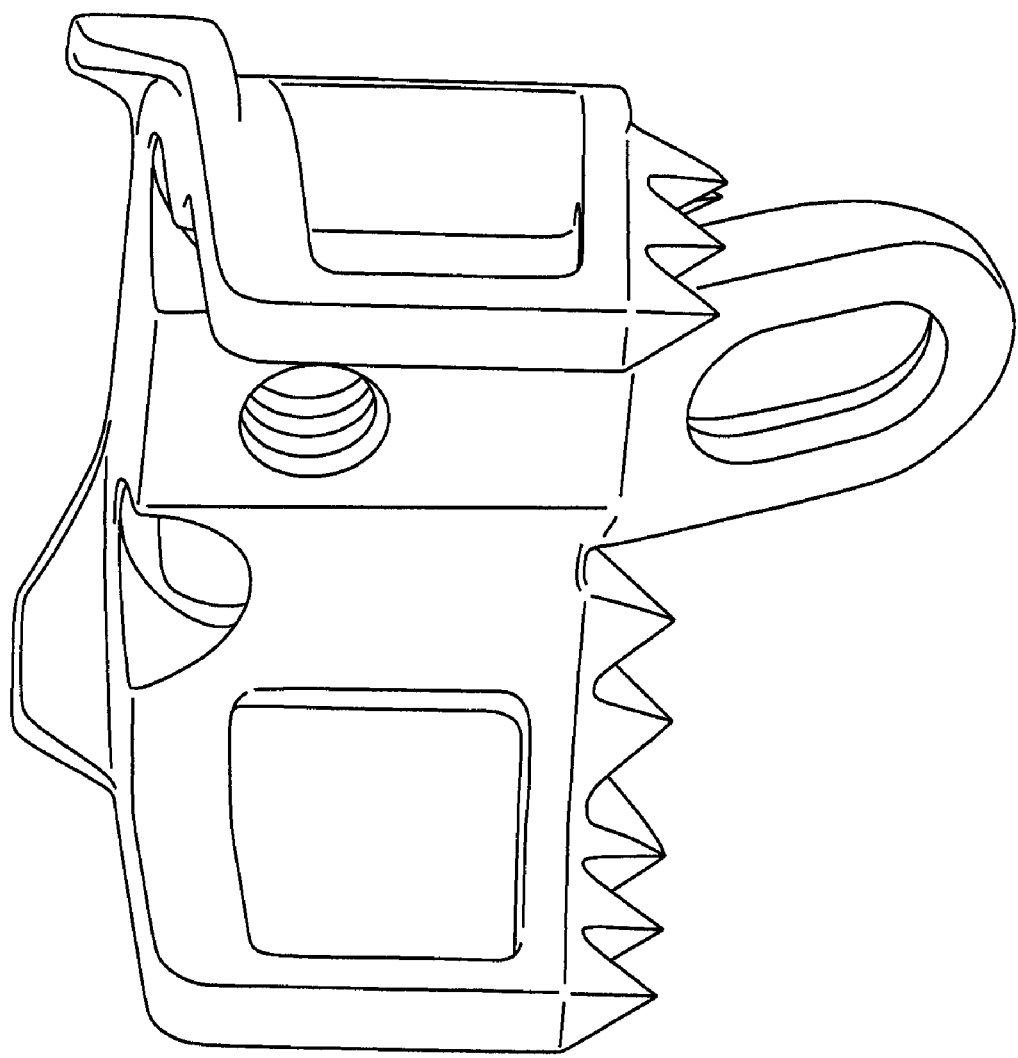
FIG. 16 is a back perspective view of another base member of an interbody device in accordance with an aspect of the present invention.

It is to be appreciated that a kit having base plates of different sizes, bone screws of differing lengths and restraining plates complementary to the base plates can be provided. For instance, because of the different physical dimensions of the patients on whom the invention is used, it is preferable that bone plate systems of correlative dimensions be available. The present invention is capable of being provided in various sizes for that purpose. FIGS. 15 and 16 illustrate examples of a base member and interbody device, respectively, having a larger size than the interbody device 10 described with respect to FIGS. 1-13. The kit may further comprise a tack tool, a drilling tool, tapping tool and/or one or more screw driving tools.

As noted above, all of the bone screws 50 may be permitted to toggle, or pivot, even after the restraining plate 60 is fixed over the base member 20. The ability of the screws 50 to toggle permits the interbody device 10 to migrate and self-center after it has been implanted.

The base member 20 is configured such that when first installed on the cervical vertebrae, the interface members 30 contact a surface of at least one of the bone bodies. For instance, in the present example, the base member 20 is positioned between the vertebrae 280 and 290 such that the top surface 150 of the base member 20 contacts an end surface of one vertebral body 280 and the interface members 30 contact an end surface of the other vertebral body 290. As discussed above, the interface members 30 are configured such that substantially immediate penetration does not occur. Rather, the interbody device 10 gradually subsides as the vertebrae and bone graft fuse to share in the weight bearing during settling of the vertebral bodies. Specifically, as the vertebral bodies move toward each other during settling, the interface members 30 will contact and enter the second vertebral body 290 with increased resistance to subsidence. This contact controls the rate of settling.

The interbody device 10 provides such an interface design by controlling the height, size, shape, and spacing of the teeth that interdigitate with the endplate of the vertebral body. In addition screw fixation is provided. The length of screw travel in the slot 180 is preferably matched to the height of the interface members 30. Accordingly, subsidence is arrested once the bone screw 50 reaches the intended limit as provided by the slot 180. Screw fixation also addresses expulsion of the interbody device, a concern common to all interbody devices. The interbody device 10 accommodates a large graft surface area further increasing the probability that fusion will occur.

The interbody device 10 as described above can have a variety of alternative configurations. Various configurations can include, but are not limited to, those shown in FIGS. 17 through 22.

Figure 17:
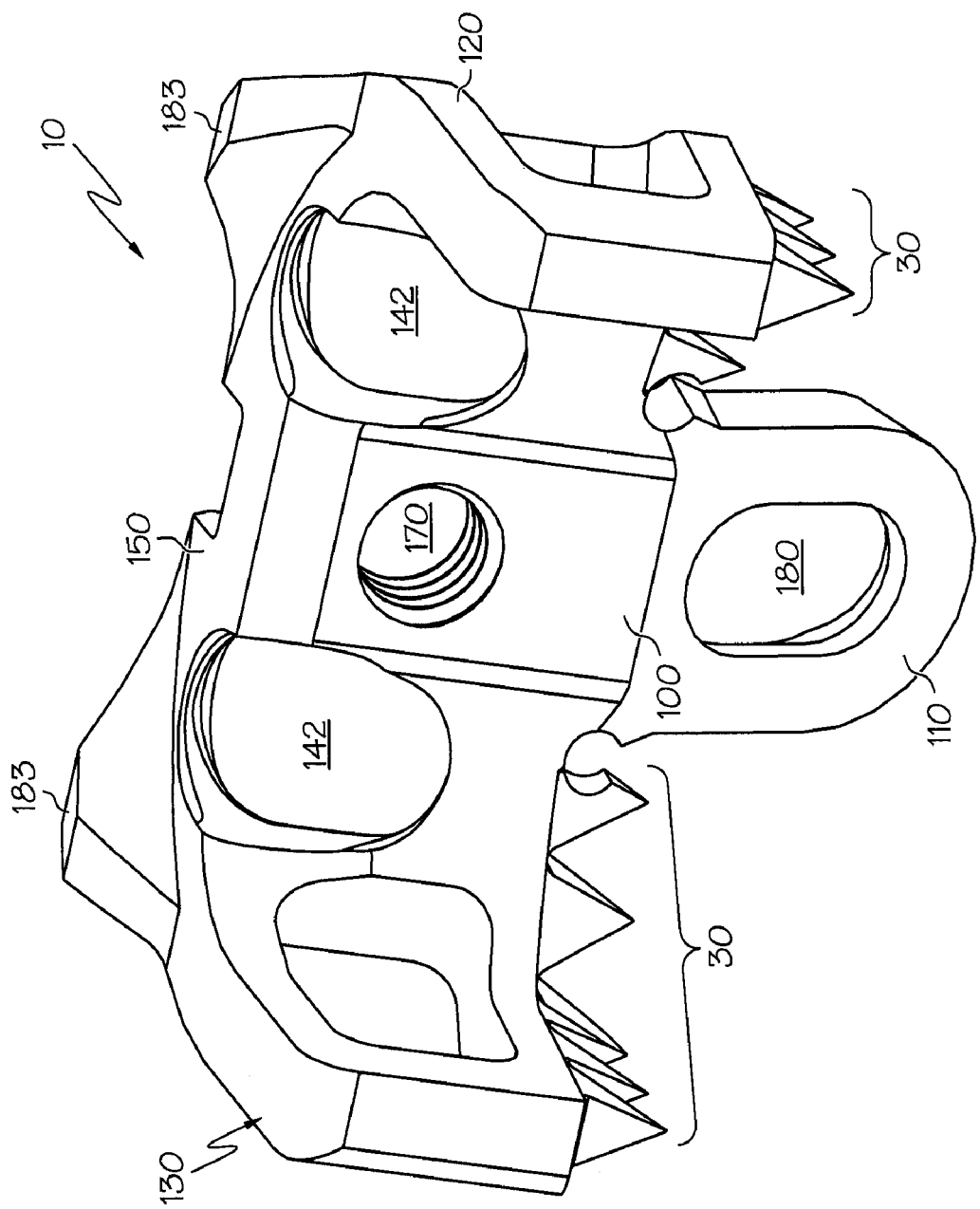
FIG. 17 is a back perspective view of a base member of an interbody device in accordance with an aspect of the present invention.

FIG. 17 illustrates an interbody device 10 comprising a base member 20 having a primary member 100 and a secondary member 110. The primary member 100 includes at least one first elongated slot 142 extending therethrough that is configured to receive a corresponding bone screw or fastener. Further, the secondary member 110 includes at least one second elongated slot 180 extending therethrough that is configured to receive a bone screw. The elongated slot 180 of the secondary member 110 is similarly referenced and described above with regard to FIGS. 4 and 5. The primary member 100 also includes a threaded hole 170 for receiving a restraining means configured to mitigate the backing out of at least one bone fastener from a bone body.

Figure 20:
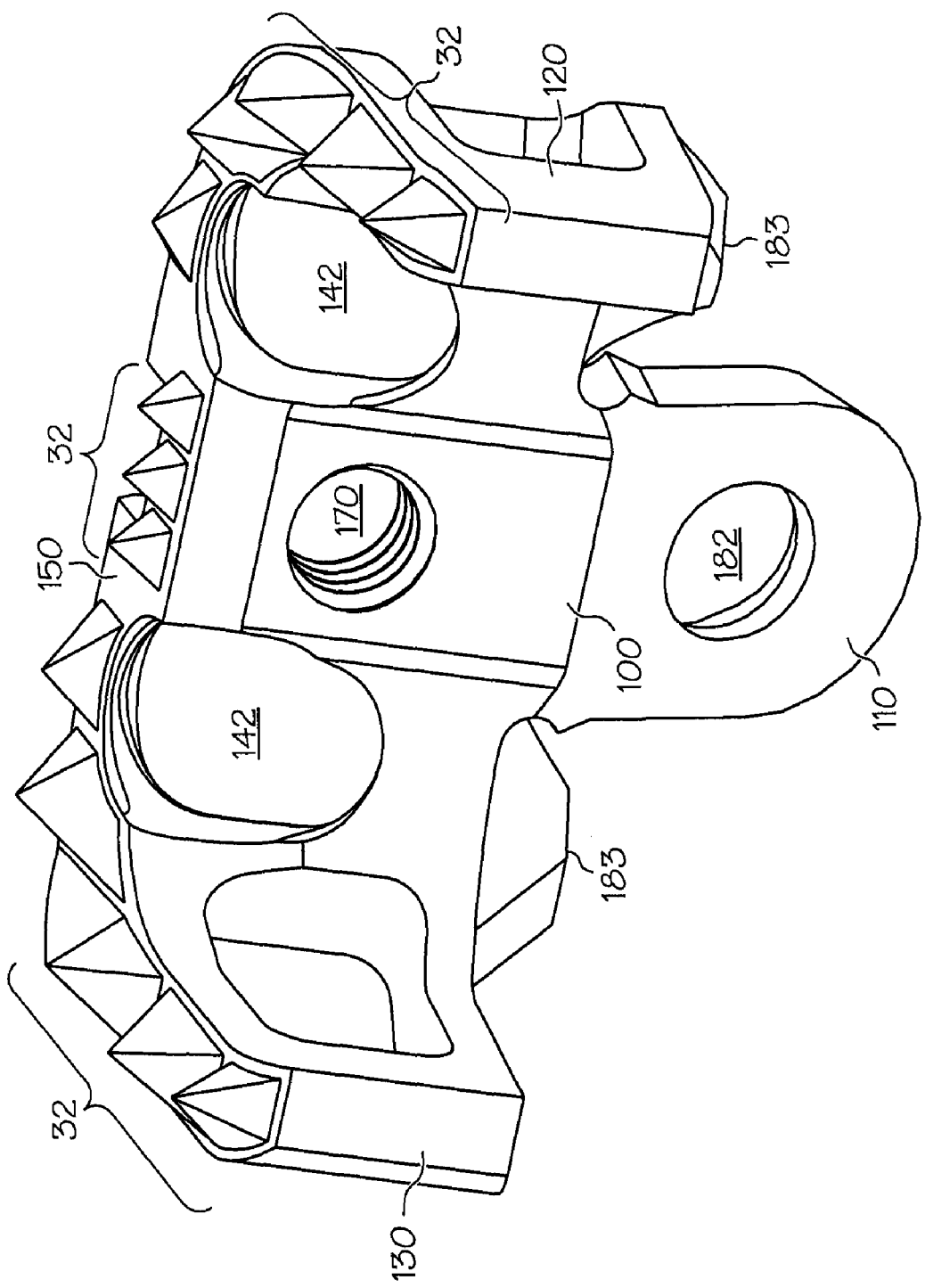
FIG. 20 is a back perspective view of a base member of an interbody device in accordance with an aspect of the present invention.

The interbody device 10 of FIG. 17 can include at least one (two are shown) projection 183 that extends upward from the top surface 150 of the primary member 100. The projection 183 provides a base or shelf that contacts a bone body in order to stop the interbody device 10 against a corresponding bone body upon insertion into a human. Although not shown in FIG. 17, the at least one projection 183 can alternatively be positioned to extend from the bottom surface of the primary member 100. In one example, FIG. 20 illustrates two projections 183 extending from the bottom surface of the primary member.

Figure 18:
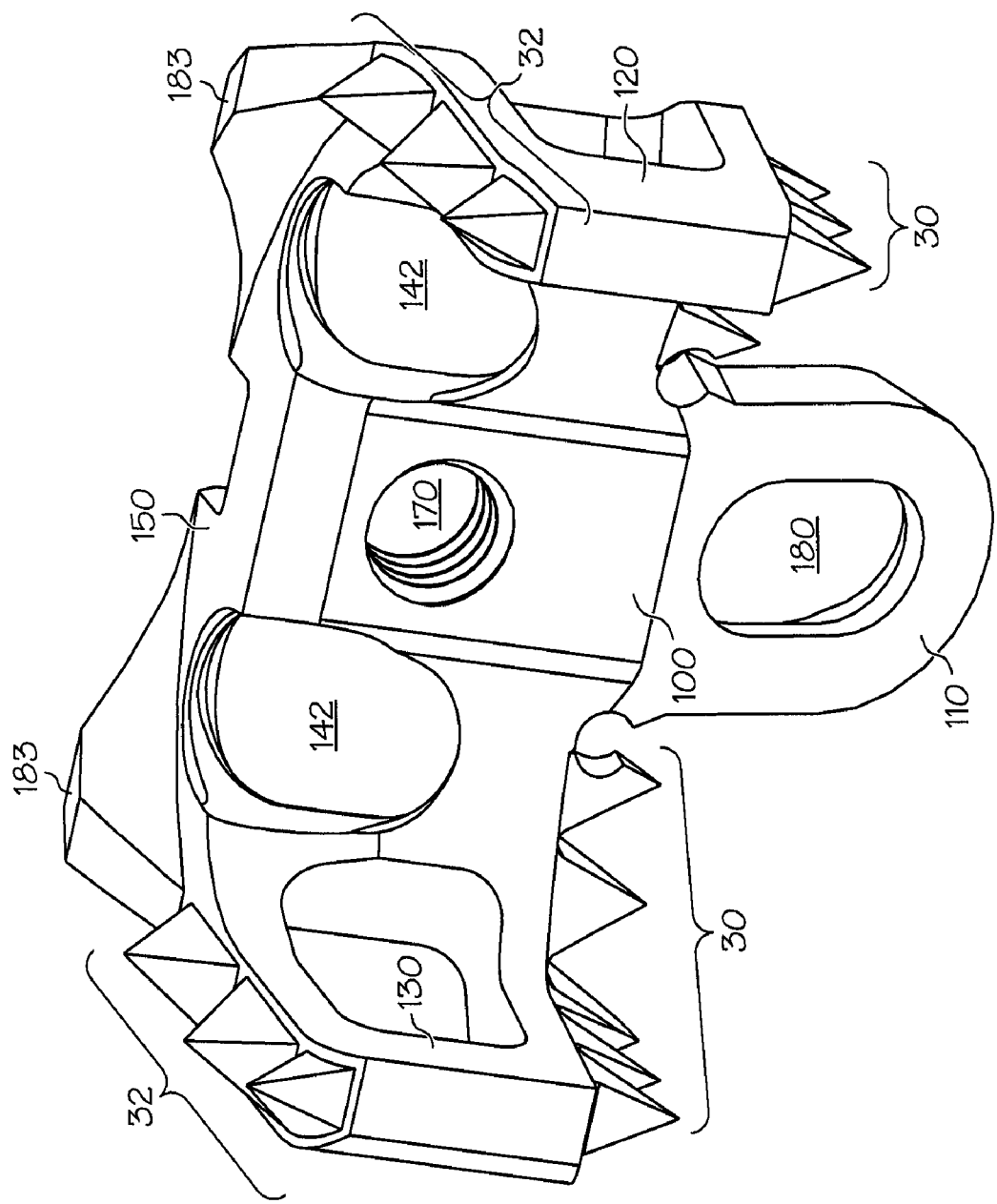
FIG. 18 is a back perspective view of a base member of an interbody device in accordance with an aspect of the present invention.

The primary member 100 of the interbody device 10 has a plurality of interface members 30 extending from the bottom surface. The interface members 30 can comprise, for example, teeth, knife-edges, spikes, posts, pegs, or combinations thereof. The interface members 30 provide a controlled subsidence interface between the interbody device 10 and a corresponding bone body. Although not shown in FIG. 17, interface members may also extend from the top surface of the primary member 100 so as to provide two controlled subsidence interfaces between the interbody device 10 and two adjacent bone bodies. In one example, FIGS. 18 and 20 illustrate various configurations of interface members 32 that may extend from the top surface of the primary member 100. To promote controlled subsidence, the interface members may extend from the top or bottom surface of the primary member 100 in a direction that is aligned with an elongate direction of two adjacent bone bodies, such as two vertebrae in a spine. For example, FIGS. 11 and 12 illustrate the interbody device 10 positioned between two adjacent bone bodies.

As illustrated in FIG. 17, the primary member 100 can have two elongated slots 142 configured such that bone screws extend through the slots 142 at an angle. Thus, each bone screw extending through the first bone screw slots 142 can enter a bone body at an angle. The elongated slots 142,180 of the primary and secondary members 100, 110 are sufficiently large to allow a portion of a bone screw, such as a threaded shaft that extends into a bone body, to pass therethrough but not large enough to allow a retaining portion of the bone screw through, such as the head of the bone screw. The general aspects of the bone screw or bone fastener are described above with regard to FIG. 8. The elongated slots 142, 180 may have a seat portion on which the retaining portion of a bone screw can rest. The seat portion of the slots 142, 180 has a generally concave spherical shape and the surface of the retaining portion of a bone screw in contact with the seat has a complementary convex spherical configuration. In this regard, the retaining portion, such as the head, of a bone screw is free to pivot on the seat of the elongated slot 142,180.

The elongated slots 142, 180 of the primary and secondary members 100, 110 in FIG. 17 are configured to permit bone screws extending therethrough to slide and rotate along the elongation length of the slots 142, 180 during controlled subsidence. In other words, the bone screws can slide relative to the interbody device 10 as the interface members 30 progressively penetrate into a corresponding bone body over time. As the bone screws slide along the elongation length of the slots 142, 180, at least one bone screw can eventually slide against the end of a slot 142, 180 it extends through. In this case, the bone screw becomes secured at the end of the corresponding slot 142, 180 such that the bone screw can no longer slide relative to the interbody device 10 as the interface members 30 may continue to penetrate into the corresponding bone body. Subsidence resistance increases as the at least one bone screw becomes secured at the end of the slot 142, 180 and can no longer slide relative to the interbody device 10. At the end of the slot 142, 180, the bone screw can toggle in order to assist the interface members 30 to further penetrate into a corresponding bone body.

Although FIG. 17 illustrates interface members 30 extending only from the bottom surface of the primary member 100, the following description of the affect the elongation length of the slots 142, 180 may have on subsidence resistance is based on interface members 30, 32 extending from the bottom and top surface of the primary member 100, for example, as illustrated in FIGS. 5, 18 and 20. Each elongated slot 142, 180 of FIG. 17 can have an elongation length that is less than, about the same as or greater than the height of at least one single interface member 30, 32. Alternatively, each elongated slot 142, 180 can have an elongation length that is less than, about the same as or greater than the height of any single interface member 30, 32.

The elongation length of the at least one slot 142 in the primary member 100 can be substantially the same as, less than or greater than the elongation length of the at least one slot 180 in the secondary member 110 depending on the desired controlled subsidence profile. Varying the elongation length of at least one slot 142, 180 can mitigate the effects that poor bone quality or an irregular surface of a bone body can have on the controlled subsidence profile. In the case that the elongation length of any one slot 142, 180 is matched to or about the same as the height of the interface members 30, 32, further subsidence resistance can occur after the bone screw slides relative to the interbody device 10 the intended limit as provided by the elongation length of the slot 142, 180. As at least one interface member 30, 32 becomes fully penetrated into a bone body, at least one bone screw becomes positioned at the end of the slot 142, 180 the screw extends through. As the bone screw rests at the end of the slot 142, 180, further subsidence resistance can occur as the bone screw toggles at the end of the slot 142, 180. The toggling of the bone screw at the end of the slot 142,180 permits the interface members 30, 32, of which some members 30, 32 may not be fully embedded in a bone body, to further penetrate into the bone body. In theory, without being bound thereto, one reason for the continued penetration of a fully-embedded interface member 30 into a bone body is poor bone quality. In another aspect, the surface of a bone body can be irregular such that a substantially flat or flush surface is not available on which the shelf-like bottom or top surface of the primary member 100 can rest. The irregular surface of a bone body can result in some of the interface members 30 not becoming fully embedded in a bone body. Depending on the degree of irregularity of a bone body surface, some of the interface members 30, 32 may also not be in contact with a bone body when the bone screw 50 slides relative to the interbody device 10 to the end the slot 142, 180. Therefore, as discussed above, toggling of the bone screw at the end of the slot 142, 180 can force the interface members 30, 32 that are not fully embedded in a bone body to penetrate further and become fully embedded.

In the case that the elongation length of any one slot 142, 180 is less than the height of the interface members 30, 32, the bone screw tends to not reach or slide to the end of the slot 142, 180 prior to any single interface member 30, 32 becoming fully embedded into a bone body. Thus, the subsidence resistance is increased when the elongation length of any one slot 142, 180 is less than the height of at least one single interface members 30, 32. In use, as the interface members 30, 32 begin to penetrate into a bone body, but before any single member becomes fully embedded, a bone screw may slide along the elongation length of the slot 142, 180 and reach the end of the slot 142, 180. Being positioned at the end of the slot 142, 180, the bone screw is forced to toggle so the interface members can further penetrate into a bone body and thus subsidence resistance is increased. In this instance, toggling of the bone screw at the end of the slot 142, 180 can assist the interface members 30, 32 that are not fully embedded in a bone body to penetrate further and become fully embedded.

In the case that the elongation length of any one slot 142, 180 is greater than the height of the interface members 30, 32, the bone screw tends to not reach or slide to the end of the slot 142, 180 prior to any single interface member 30, 32 becoming fully embedded into a bone body. Increasing the length a bone screw can travel or slide in a slot 142, 180 can decrease subsidence resistance. For example, an irregular bone body surface can cause at least one interface member 30, 32 to become fully embedded in a bone body before a bone screw slides relative to the interbody device 10 to the end of the slot 142, 180. The bone screw in this instance can continue to slide along the elongation length of the slot 142, 180 as the remaining interface members 30, 32 continue to further penetrate into a bone body surface. The additional distance or length the bone screw 50 can travel before reaching the end of the slot 142, 180 generally makes it unnecessary for the bone screw 50 to toggle in slot 142, 180 to ensure that the interface members 30, 32 become fully embedded in a bone body. The subsidence resistance profile in this case would be substantially lower because, in part, the bone screw generally does not need to toggle in the slot 142, 180 in order to ensure the interface members 30, 32 become fully embedded. Further, the bone screw 50 in this case will not generally rest at the end of the slot 142, 180, which can increase the subsidence resistance.

In another aspect, the elongation length of any one slot 142, 180 of the interbody device 10 of FIG. 17 can be substantially zero. The slot 142, 180 in this instance tends to function substantially the same as a bone screw hole as described above, for example, with regard to hole 140 of FIGS. 4 and 5. Thus, the slot 142, 180 has substantially no elongation over which a bone screw can travel along. In this regard, a bone screw is forced to toggle in the slot 142, 180 to assist penetration of the interface members 30, 32 into at least one bone body and thus subsidence resistance is increased in this configuration. That is, a stiff construct comprising at least one bone body and the interbody device 10 results from the elongation length of any one slot 142, 180 being substantially zero.

As can be seen above with regard to the interbody device 10 of FIG. 17, the subsidence resistance profile can be controlled and/or affected by the combination of the elongation length of any single slot 142, 180 and the shape, location and height of the interface members 30, 32. Each of these features of the present invention can be adjusted, modified or combined in order to compensate for poor bone quality, an irregular surface of a bone body or to ensure full penetration of the interface members 30, 32 into at least one bone body.

Turning to FIG. 18, the interbody device 10 can have interface members 32 on the top surface of the first and second legs 120, 130 of the primary member 100. The interbody device 10 can further have interface members 30 extending from the bottom surfaces of the primary member 100, the first leg 120 and the second leg 130. FIG. 19 illustrates interface members 30, 32 extending from the top and bottom surface of a representative leg of the primary member 100. Although not shown in FIG. 18, the interbody device 10 can have additional interface members 32 which extend upward from the top surface 150 of the primary member 100. In one example, FIG. 20 illustrates interface members 32 extending upward from the top surface 150 of the primary member 100. The interbody device 10 of FIG. 18 has at least one bone screw slot 142 in the primary member 100 and at least one bone screw slot 180 in the secondary member 110. As shown, FIG. 18 illustrates two bone screw slots 142 in the primary member 100 and one bone screw slot 180 in the secondary member 110. In this embodiment, the interbody device 10 provides controlled subsidence at the interface of the top interface members 32 with a corresponding bone body and at the interface of the bottom interface members 30 with a corresponding bone body. The primary member 100 also includes a threaded hole 170 for receiving a restraining means configured to mitigate the backing out of at least one bone fastener from a bone body.

Each elongated slot 142, 180 of FIG. 18 can have an elongation length that is less than, about the same as or greater than the height of at least one single interface member 30, 32. Further, each elongated slot 142, 180 can have an elongation length that is less than, about the same as or greater than the height of any single interface member 30, 32. The at least one slot 142 in the primary member 100 and at least one slot 180 in the secondary member 110 can have about the same or varying elongation lengths depending on the desired controlled subsidence profile. As discussed above with regard to FIG. 17, the elongation length of each slot 142, 180 in the interbody device 10 of FIG. 18 can also be modified to increase or decrease the subsidence resistance as the interface members 30, 32 penetrate into corresponding bone bodies.

In one aspect, the height of the interface members 30, 32 may be about half of the overall desired controlled subsidence distance. For example, if it is desirable to have a total of 2 mm of penetration into the corresponding bone bodies, the top interface members 32 and bottom interface members 30 may each respectively have a height of about 1 mm. In another aspect, the interface members 30, 32 may each respectively have about 1 to 99 percent of the overall desired subsidence control. In yet another aspect, interface members 32 can be located on only the top surface of the first leg 120, second leg 130 or primary member 100 (see FIG. 20) or the interface members 30 can be located on only the bottom surface of the first and second legs 120, 130 or the primary member 100 (not shown). In this case, controlled subsidence would only occur at the interface of the top members 32 and a corresponding bone body or at the interface of the bottom members 30 and a corresponding bone body.

FIG. 20 illustrates an interbody device 10 having a pair of elongated slots 142 extending through the primary member 100. The interface members 32 of the device 10 extend from the top surface of the primary member 100 and first and second legs 120, 130. The secondary member 110 has a single bone screw hole 182 configured for receiving a bone screw. Projections 183 extend from the bottom surface of the primary member 100 and provide a shelf or surface to stop the interbody device 10 against a bone body upon insertion into a spine. The projections 183 may be positioned on the bottom surface of the primary member 100 in order to increase the area on the top surfaces 150 of the primary member 100 and first and second legs 120, 130 on which the interface members 32 may be located.

Figure 21:
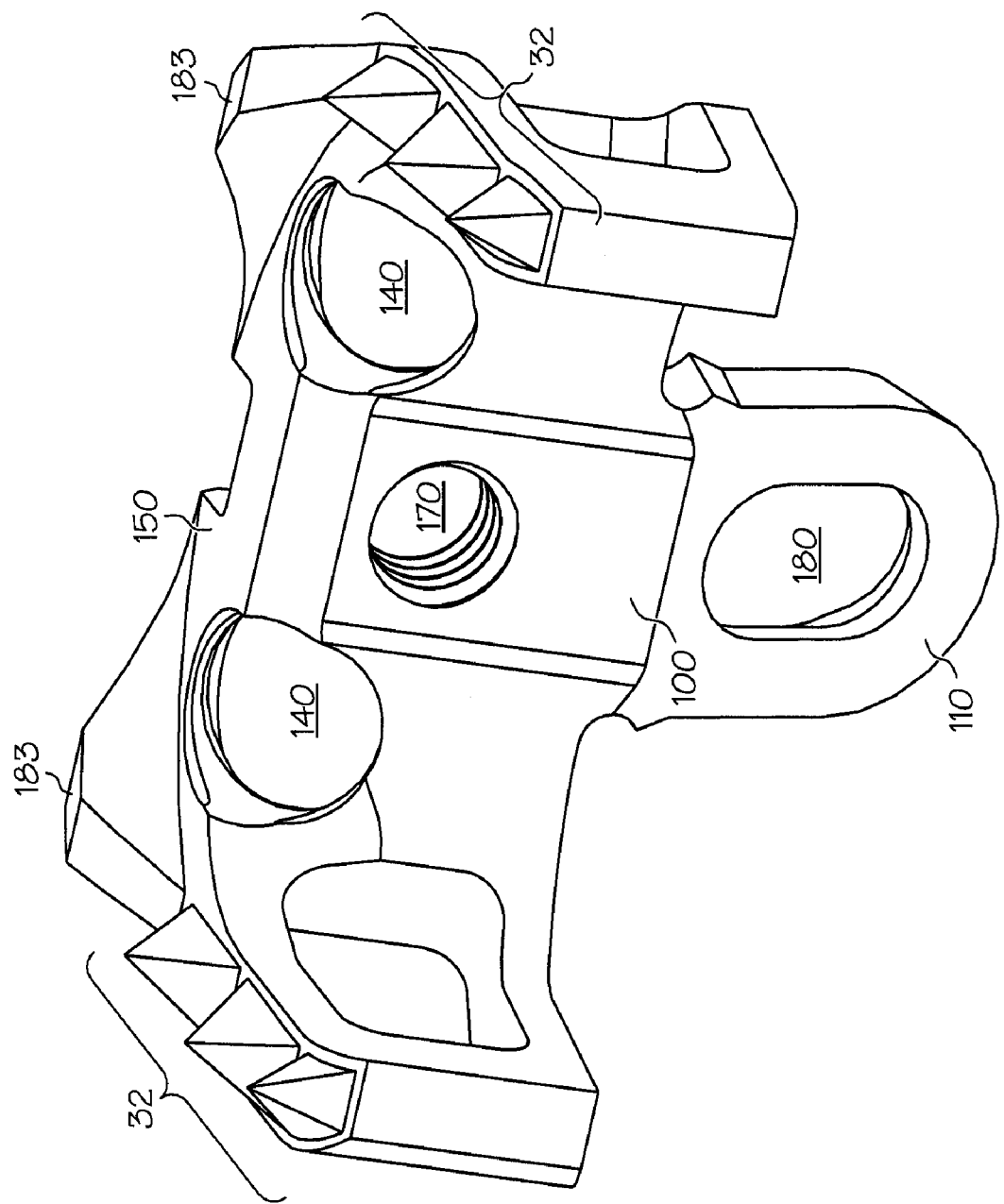
FIG. 21 is a back perspective view of a base member of an interbody device in accordance with an aspect of the present invention.

In another aspect, the single screw hole 182 in the secondary member 110 of the interbody device 10 of FIG. 20 may be an elongated slot 180 and the pair of elongated slots 142 of the primary member 100 may be a pair of screw holes 140. For example, the interbody device 10 of FIG. 21 illustrates an interbody device 10 having two bone screw holes 140 in the primary member 100 and an elongated slot 180 in the secondary member 110. The primary member 100 also may include a threaded hole 170 for receiving a restraining means configured to mitigate the backing out of at least one bone fastener from a bone body.

Figure 22:
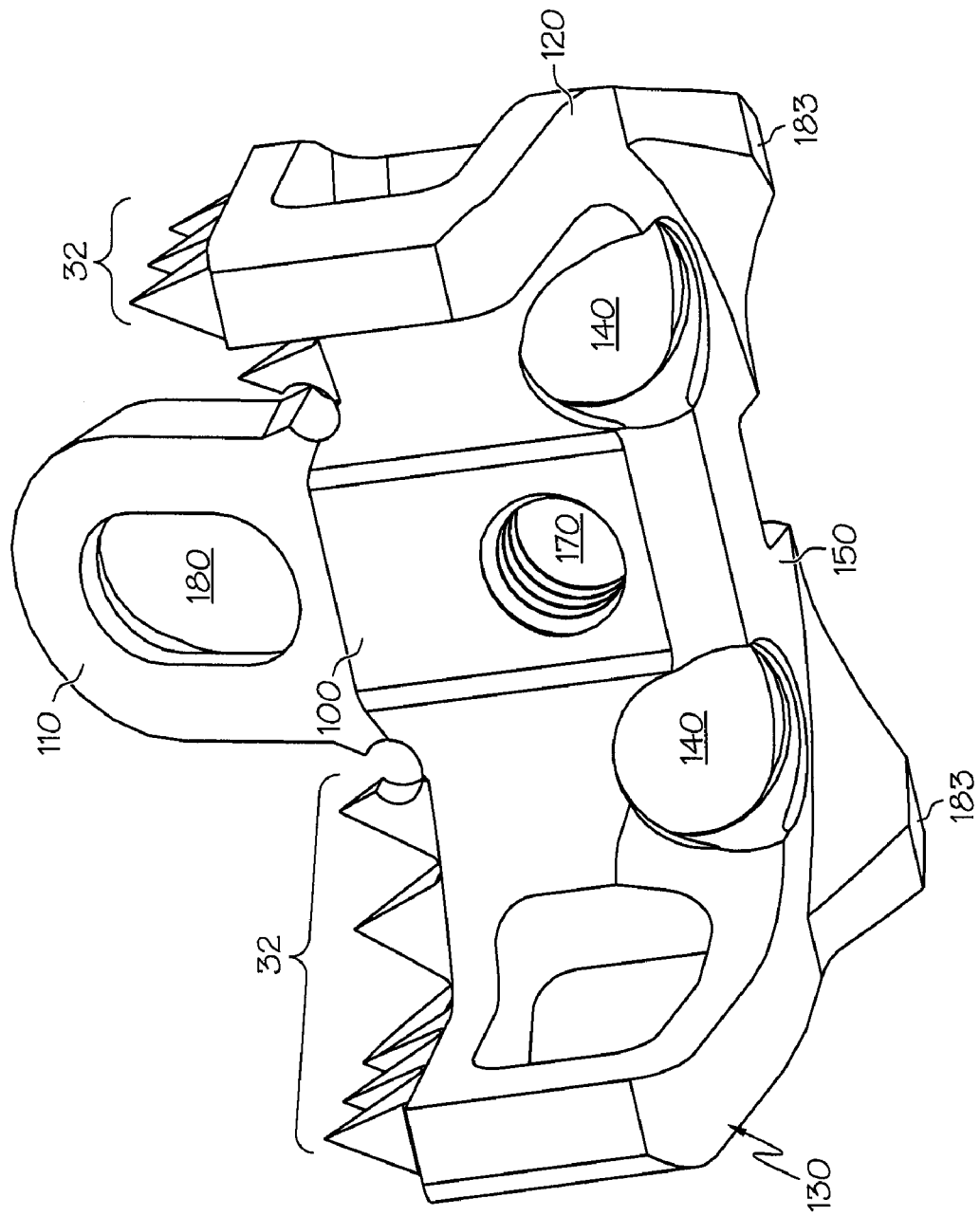
FIG. 22 is a back perspective view of a base member of an interbody device in accordance with an aspect of the present invention.

FIG. 22 illustrates yet another alternative configuration of the interbody device 10. The interbody device 10 of FIG. 22 may be configured for insertion into a spine such that the secondary member 110 extends upward from a surface of the primary member 100. That is, FIG. 22 illustrates an inverted view of the interbody device 10 shown in the other Figures herein. The interface members 32, which generally extend downward as representatively shown in FIGS. 17 through 21, extend upward in the direction of the secondary member 110. In this embodiment, the interbody device 10 provides controlled subsidence at the interface of the top interface members 32 and a corresponding bone body. The primary member 100 and secondary member 110 are arranged relative to each other so that their front surfaces at their interface form an angle greater than 90° and less than 180°, or about 110° to about 160°. As shown, the primary member 100 can include at least one bone screw hole 140 and the secondary member 110 can include at least one elongated slot 180. The elongated slot 180 can have an elongation length that is less than, about the same as or greater than the height of at least one single interface member 32. Alternatively, the elongated slot 180 can have an elongation length that is less than, about the same as or greater than the height of any single interface member 32. As discussed above with regard to FIG. 17, the elongation length of slot 180 in the interbody device 10 of FIG. 22 can be modified to increase or decrease the subsidence resistance as the interface members 32 penetrate into a bone body. Further, as shown in the Figures herein, the primary member 100 may also include a threaded hole 170 for receiving a restraining means configured to mitigate the backing out of at least one bone fastener from a bone body.

Although not shown in FIG. 22, the interbody device 10 can have additional interface members extending from a bottom surface of the primary member 100, for example, as illustrated in FIGS. 18 and 20. In another aspect, the secondary member 110 may include an aperture other than the elongated slot 180 shown, such a bone screw hole as shown in FIG. 20. In yet another aspect, the primary member 100 may include an aperture other than the bone screw holes 140 shown, such as an elongated slot as shown in FIGS. 17 and 18.

In another embodiment, the various configurations of the interbody device 10, including but not limited to those shown in FIGS. 17 through 22, may include a plurality of interface members of any desirable height and shape. In one example, as shown in FIG. 17, each of the plurality of interface members 30 extending upward from the surface of the primary member 100 can have the same height. Alternatively, the plurality of interface members 30 of FIG. 17 may have different heights such that at least one of the plurality of members 30 extending from the primary member 100 has a height substantially not equal to at least one other interface member 30 (not shown). In this regard, the profile of interface members 30 extending from a surface of the primary member 100 may be varied or contoured to the surface of a corresponding bone body, such as an irregular or substantially non-flush surface for the interbody device 10 to rest upon. The shape and height of the plurality of interface members 30 may be modified to fit into or conform with the irregularities of a bone body surface, such a peaks, bumps, cavities, voids and the like. Such irregularities may reduce the number of interface members 30 which fully penetrate a bone body and the depth to which interface members 30 may become embedded. Thus, irregular bone body surfaces provide different controlled subsidence profiles.

While shown embodiments of the present invention are described for supporting adjacent cervical vertebrae in the anterior region of the vertebrae, persons skilled in the art would recognize that the bone pate of the present invention may be utilized to support adjoining thoracic and lumbar vertebrae in the lateral or posterior regions of the vertebrae. Further, the device and method of the invention is not limited to vertebral bodies, but can also be use to join two other pieces of bone in other parts of the body.

While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An interbody device comprising:
   a u-shaped base member comprising a primary member and a secondary member, wherein the primary member being integrally formed with first and second legs and having a top surface and a bottom surface, and the secondary member extending at an angle relative to the primary member and downward from the bottom surface of the primary member;
   said first and second legs of said primary member being spaced laterally from each other to extend around an open area there between for receiving bone graft material, said primary member having a plurality of interface members extending from at least one surface thereon with at least a portion of the interface members being located at the first and second legs, the interface members being configured to provide controlled subsidence of the interbody device subsequent to implantation via penetration of the interface members into at least one bone body at locations not at the open area between the first and second legs;
   said primary member having at least one angled aperture, wherein the at least one angled aperture comprises an elongated slot configured to receive a bone fastener therethrough;
   said secondary member having at least one angled aperture configured to receive a bone fastener therethrough, and
   a plurality of bone fasteners extending through said apertures in said primary and secondary members of the base member.

2. The interbody device of claim 1, wherein the plurality of interface members extend from the top surface and the bottom surface of the primary member, with at least some of the interface members being at the first and second legs, and at least some of the interface members being at a portion of the u-shape extending between the first and second legs and located at an anterior side adjacent to locations of the plurality of bone fasteners extending through said apertures in said primary and secondary members.

3. The interbody device of claim 1, wherein the plurality of interface members extend from the top surface of the primary member.

4. The interbody device of claim 1, wherein at least some of the interface members being at the first and second legs, and at least some of the interface members being at a portion of the u-shape extending between the first and second legs and located at an anterior side adjacent to locations of the plurality of bone fasteners extending through said apertures in said primary and secondary members.

5. The interbody device of claim 1, wherein the relative sliding movement occurs between at least one of the plurality of bone fasteners and the base member during controlled subsidence.

6. The interbody device of claim 1, wherein the interface members extend from the top surface and the bottom surface of the primary member and in a direction that is aligned with an elongate direction of the spine.

7. The interbody device of claim 6, wherein the interface members progressively penetrate into at least one bone body over a period of time subsequent to the implantation of the interbody device.

8. The interbody device of claim 6, wherein the at least one angled aperture through the secondary member comprises an elongated slot, the at least one elongated slot extending through the primary member and the at least one elongated slot extending through the secondary member permit the bone fasteners extending therethrough to travel along the elongated slots as the interface members extending from the top surface and the bottom surface of the primary member penetrate into at least one bone body during the controlled subsidence over a period of time subsequent to the implantation of the interbody device, wherein at least one of the elongated slots has an elongation length greater than the height of at least one single interface member.

9. The interbody device of claim 8, wherein at least one of the elongated slots has an elongation length greater than the height of any single interface member.

10. The interbody device of claim 8, wherein relative sliding movement occurs between the at least one of the plurality of bone fasteners and the base member as the interface members penetrate.

11. The interbody device of claim 8, wherein at least one interface member is substantially fully penetrated into at least one bone body during the controlled subsidence and at least one bone fastener is not at the end of the elongated slot through which said bone fastener extends.

12. The interbody device of claim 8, wherein the height of the interface members extending from the top surface of the primary member are about the same height of the interface members extending from the bottom surface of the primary member.

13. The interbody device of claim 12, wherein the height of the interface members is less than the elongation length of the at least one elongated slot extending through the primary member and the elongation length of at least one elongated slot extending through the secondary member so that the bone fasteners extending through the elongated slots do not reach the end of the elongated slots as the interface members fully penetrate into a corresponding bone body.

14. The interbody device of claim 6, wherein the at least one angled aperture through the secondary member comprises an elongated slot, the at least one elongated slot extending through the primary member and the at least one elongated slot extending through the secondary member permit the bone fasteners extending therethrough to travel along the elongated slots as the interface members extending from the top surface and the bottom surface of the primary member penetrate into at least one bone body during the controlled subsidence over a period of time subsequent to the implantation of the interbody device, wherein at least one of the elongated slots has an elongation elongation length less than the height of at least one interface member.

15. The interbody device of claim 14, wherein at least one of the elongated slots has an elongation length less than the height of any single interface member.

16. The interbody device of claim 14, wherein the relative sliding movement occurs between at least one of the plurality of bone fasteners and the base member as the interface members penetrate.

17. The interbody device of claim 14, wherein at least one bone fastener is at the end of at least one of the elongated slots through which said bone fastener extends before at least one interface member is substantially fully penetrated into a corresponding bone body during the controlled subsidence.

18. The interbody device of claim 17, wherein the bone fastener at the end of the elongated slot toggles in said elongated slot to permit the interface members to further penetrate into a corresponding bone body.

19. The interbody device of claim 14, wherein the height of the interface members extending from the top surface of the primary member are the about the same height of the interface members extending from the bottom surface of the primary member.

20. The interbody device of claim 19, wherein the height of the interface members is greater than the elongation length of the at least one elongated slot extending through the primary member and the at least one elongated slot extending through the secondary member, wherein the bone fasteners slide along the elongated slots, and the bone fasteners reach the end of the elongated slots before at least one of the interface members fully penetrates into a corresponding bone body.

21. The interbody device of claim 1, wherein the at least one aperture in the secondary member includes a hole configured to receive a bone fastener therethrough.

22. The interbody device of claim 21, wherein the plurality of interface members extend from the top surface and the bottom surface of the primary member.

23. The interbody device of claim 21, wherein the plurality of interface members extend from the top surface of the primary member.

24. The interbody device of claim 21, wherein at least some of the interface members extend from the bottom surface of the primary member and at least some of the interface member being at a portion of the u-shape extending between the first and second legs and located at an anterior side adjacent to locations of the plurality of bone fasteners extending through said apertures in said primary and secondary members.

25. The interbody device of claim 21, wherein the interface members extend from at least one of the said surfaces of the primary member in a direction that is aligned with an elongate direction of the spine.

26. The interbody device of claim 25, wherein the at least one elongated slot extending through the primary member permits the bone fastener extending therethrough to travel along the elongated slot as the interface members extending from the at least one surface of the primary member penetrate into at least one bone body during the controlled subsidence over a period of time subsequent to the implantation of the interbody device, wherein the at least one elongated slot has an elongation length greater than the height of at least one single interface member.

27. The interbody device of claim 26, wherein the at least one elongated slot has an elongation length is greater than the height of any single interface member.

28. The interbody device of claim 26, wherein at least one interface member is substantially fully penetrated into a corresponding bone body during the controlled subsidence and at least one bone fastener is not at the end of the elongated slot through which said bone fastener extends.

29. The interbody device of claim 26, wherein the height of the interface members is less than the elongation length of the at least one elongated slot extending through the primary member so that the bone fastener extending through the elongated slot slides along the elongation length of the elongated slot, and the bone fastener does not reach the end of the elongated slot as at least one of the interface members fully penetrates into a corresponding bone body.

30. The interbody device of claim 25, wherein the at least one elongated slot extending through the primary member permits the bone fastener extending therethrough to travel along the elongation length of the slot as the interface members extending from at least one surface of the primary member penetrate into a bone body during the controlled subsidence over a period of time subsequent to the implantation of the interbody device, wherein at least one elongated slot has an elongation length less the height of at least one single interface member.

31. The interbody device of claim 30, length less than elongated slot has an elongation length is less than the height of any single interface member.

32. The interbody device of claim 30, wherein at least one bone fastener is at the end of the elongated slot through which said bone fastener extends before at least one interface member is substantially fully penetrated into at least one bone body during controlled subsidence.

33. The interbody device of claim 30, wherein the height of the interface members is greater than the elongation length of the at least one elongated slot extending through the primary member, wherein the bone fastener slides along the elongation length of the elongated slot, and the bone fastener reachs the end of the elongated slot before at least one of the interface members fully penetrates into a corresponding bone body.

34. The interbody device of claim 1, wherein the controlled subsidence includes at least one bone fastener sliding relative to the base member in the elongated slot the bone fastener extends through at a distance substantially equal to the depth of penetration of at least one of the interface members into a bone body, wherein the depth of penetration of the at least one interface member is substantially equal to the height of the interface member, and said bone fastener not being at the end of the elongated slot.

35. The interbody device of claim 1, wherein the controlled subsidence includes at least one bone fastener sliding relative to the base member in the elongated slot the bone fastener extends through at a distance substantially less than the depth of penetration of at least one of the interface members into a bone body, wherein the depth of penetration of the interface member is substantially equal to the height of the interface member, and said bone fastener being at the end of the elongated slot.

36. The interbody device of claim 1, wherein the controlled subsidence includes at least one bone fastener sliding relative to the base member to the end of the elongated slot the bone fastener extends through during the penetration of at least one interface member into a bone body, wherein the bone fastener toggles at the end of the elongated slot before the interface member is fully embedded into the bone body.

37. The interbody device of claim 1, wherein at least one elongated slot extending through the primary member has an elongation length that permits a bone fastener extending therethrough to slide along the elongation length of the elongated slot, wherein the elongation length of the elongated slot is substantially equal to the height of the interface members.

38. The interbody device of claim 1, wherein at least one of the plurality of interface members extending from at least one surface of the base member has a height substantially not equal to at least one other interface member.

39. The interbody device of claim 1, further comprising a retaining plate secured to the base member via a fastener to mitigate the backing out of a bone fastener, wherein the restraining plate is configured to permit at least one bone fastener to slide and toggle in the aperture the bone fastener extends through.

40. The interbody device of claim 1, further comprising a restraining means for mitigating the backing out of at least one bone fastener from a bone body.

41. An interbody device comprising:
  a u-shaped base member comprising a primary member and a secondary member, wherein the primary member being integrally formed with first and second legs and having a top surface and a bottom surface, and the secondary member extending at an angle relative to the primary member and downward from the bottom surface of the primary member;

said first and second legs of said primary member being spaced laterally from each other to extend around an open area there between for receiving bone graft material, said primary member having a plurality of interface members extending from at least one surface thereon with at least a portion of the interface members being located at the first and second legs, the interface members being configured to provide controlled subsidence of the interbody device subsequent to implantation via penetration of the interface members into at least one bone body at locations not at the open area between the first and second legs;

said primary member having at least one angled aperture, wherein the at least one angled aperture comprises a hole configured to receive a bone fastener therethrough;

said secondary member having at least one angled aperture, wherein the at least one angled aperture comprises a hole configured to receive a bone fastener therethrough; and a plurality of bone fasteners extending through said apertures in said primary and secondary members of the base member;

wherein at least one of the holes is an elongate slot.

42. The interbody device of claim 41, wherein the hole extending through the primary member and the hole extending through the secondary member each have a generally concave spherical seat to permit the bone fastener extending therethrough to pivot on the seat and toggle in the hole.

43. The interbody device of claim 42, wherein the bone fasteners toggles in the holes as the plurality of interface members penetrate into the at least one bone body.

44. The interbody device of claim 41, wherein at least one bone fastener comprises a portion adapted to be substantially secured in a bone body and a retaining portion, the diameter of the portion secured in a bone body being substantially less than the diameter of the hole so that the portion secured in a bone body can slide in the hole during the controlled subsidence as the interface members penetrate into at least one bone body.

45. The interbody device of claim 41, further comprising a restraining means for mitigating the backing out of at least one bone fastener from a bone body.

46. The interbody device of claim 41, wherein the interface members extend from the top surface and the bottom surface of the primary member.

47. The interbody device of claim 41, wherein at least some of the interface member being at a portion of the u-shape extending between the first and second legs and located at an anterior side adjacent to locations of the plurality of bone fasteners extending through said apertures in said primary and secondary members.

48. The interbody device of claim 41, wherein the interface members extend from the bottom surface of the primary member.

49. The interbody device of claim 41, wherein the holes of the base member are configured to permit the permit the bone fasteners extending therethrough to toggle within the holes.

50. An interbody device comprising:
a u-shaped base member comprising a primary member and a secondary member, wherein the primary member being integrally formed with first and second legs and having a top surface and a bottom surface, and the secondary member extending at an angle relative to the primary member and upward from the top surface of the primary member;

said first and second legs of said primary member being spaced laterally from each other to extend around an open area there between for receiving bone graft material, said primary member having a plurality of interface members extending from at least one surface thereon with at least a portion of the interface members being located at the first and second legs, the interface members being configured to provide controlled subsidence of the interbody device subsequent to implantation via penetration of the interface members into at least one bone body at locations not at the open area between the first and second legs;

said primary member having at least one angled aperture configured to receive a bone fastener therethrough;

said secondary member having at least one angled aperture configured to receive a bone fastener therethrough; and a plurality of bone fasteners extending through said apertures in said primary and secondary members of the base member;

wherein at least one of the holes is an elongate slot.

51. The interbody device of claim 50, further comprising a restraining means for mitigating the backing out of at least one bone fastener from a bone body.

52. The interbody device of claim 50, wherein the plurality of interface members extend from the top surface and the bottom surface of the primary member.

53. The interbody device of claim 50, wherein the plurality of interface members extend from the top surface of the primary member.

54. The interbody device of claim 50, wherein the plurality of interface members extend from the bottom surface of the primary member.

55. The interbody device of claim 50, wherein the relative sliding movement occurs between at least one of the plurality of bone fasteners and the base member during controlled subsidence.

56. The interbody device of claim 50, wherein the at least one aperture in the primary member comprises a hole configured to receive a bone fastener therethrough.

57. The interbody device of claim 50, wherein the at least one aperture in the secondary member comprises an elongated slot configured to receive a bone fastener therethrough.

58. The interbody device of claim 50, wherein the at least one aperture in the secondary member comprises a hole configured to receive a bone fastener therethrough.

* * * * *

UNITED STATES PATENT AND TRADEMARK OFFICE
CERTIFICATE OF CORRECTION

PATENT NO.         : 8,100,976 B2
APPLICATION NO.    : 11/620255
DATED              : January 24, 2012
INVENTOR(S)        : Robert Bray et al.

Page 1 of 1

It is certified that error appears in the above-identified patent and that said Letters Patent is hereby corrected as shown below:

Column 19, line 52, claim 5, please delete "the";
Column 22, line 2, claim 31, please delete "is";
Column 24, line 43, claim 55, please delete "the"

Signed and Sealed this
Tenth Day of April, 2012

David J. Kappos
*Director of the United States Patent and Trademark Office*